United States Patent
Calco et al.

(10) Patent No.: US 11,478,374 B2
(45) Date of Patent: Oct. 25, 2022

(54) CERVICAL COLLAR HAVING HEIGHT ADJUSTMENT

(71) Applicant: Ossur Iceland ehf, Reykjavik (IS)

(72) Inventors: Wayne Calco, Foothill Ranch, CA (US); Christopher Callicott Webster, Foothill Ranch, CA (US); Harry Duane Romo, Foothill Ranch, CA (US)

(73) Assignee: OSSUR ICELAND EHF, Reykjavik (IS)

( * ) Notice: Subject to any disclaimer, the term of this patent is extended or adjusted under 35 U.S.C. 154(b) by 392 days.

(21) Appl. No.: 16/686,582

(22) Filed: Nov. 18, 2019

(65) Prior Publication Data
US 2020/0085607 A1      Mar. 19, 2020

Related U.S. Application Data

(63) Continuation of application No. 15/442,029, filed on Feb. 24, 2017, now Pat. No. 10,512,559.
(Continued)

(51) Int. Cl.
*A61F 5/055*      (2006.01)
*A61F 5/01*       (2006.01)

(52) U.S. Cl.
CPC ...... *A61F 5/055* (2013.01); *A61F 2005/0197* (2013.01)

(58) Field of Classification Search
CPC ............... A61F 5/055; A61F 5/05883; A61F 2250/0004; A61F 5/3707; A61F 5/05891; A61F 2007/0011; A61F 5/012; A61F 13/12; A61F 5/028; A61F 13/128; A61F 5/05816; A42B 3/0473
See application file for complete search history.

(56) References Cited

U.S. PATENT DOCUMENTS 2,088,207 A    7/1937   Kaiser
2,102,069 A    12/1937  Hanicke
(Continued)

FOREIGN PATENT DOCUMENTS

CN    1646071 A    7/2005
CN    2933343 Y    8/2007
(Continued)

OTHER PUBLICATIONS

Office Action from corresponding CN Application No. 201780057654.X, dated Oct. 29, 2020.
(Continued)

*Primary Examiner* — Ophelia A Hawthorne
(74) *Attorney, Agent, or Firm* — Workman Nydegger

(57) ABSTRACT

A cervical collar has an anterior component including a lower support that is adjustable in angle relative to a main support. The lower support is hingedly connected to the main support at first and second end portions. An elongate element engages the first and second end portions. A lock mechanism is operatively connected to the elongate element, and is arranged for locking rotation of the lower support relative to the main support, by moving the elongate element between locked and unlocked conditions. An upper support is received by the main support at least at a front section of the main support, and is arranged to be fitted against a user's chin.

15 Claims, 20 Drawing Sheets

Related U.S. Application Data

(60) Provisional application No. 62/299,766, filed on Feb. 25, 2016.

(56) References Cited

U.S. PATENT DOCUMENTS

| | | |
|---|---|---|
| 2,735,424 A | 2/1953 | Benjamin |
| 2,791,999 A | 5/1954 | Bustamante |
| 2,801,630 A | 8/1957 | Moore |
| 2,806,471 A | 11/1957 | Breese |
| 2,818,063 A | 12/1957 | Smith et al. |
| 2,820,455 A | 1/1958 | Hall |
| 2,911,970 A | 11/1959 | Bartels |
| D188,302 S | 6/1960 | Monfardini |
| 3,024,784 A | 3/1962 | Monfardini |
| 3,027,894 A | 4/1962 | Moore |
| 3,042,027 A | 7/1962 | Monfardini |
| 3,050,052 A | 8/1962 | Grassl |
| 3,060,930 A | 10/1962 | Grassl |
| 3,075,521 A | 1/1963 | Grassl |
| 3,135,256 A | 6/1964 | Gruber |
| 3,177,869 A | 4/1965 | Bartels |
| D203,018 S | 11/1965 | Helferich |
| 3,285,243 A | 11/1966 | Yellin |
| 3,285,244 A | 11/1966 | Cottrell |
| 3,306,284 A | 2/1967 | McKinley |
| 3,313,297 A | 4/1967 | Applegate et al. |
| 3,320,950 A | 5/1967 | McElvenny |
| 3,504,667 A | 4/1970 | McFarlane |
| 3,512,523 A | 5/1970 | Barnett |
| 3,756,226 A | 9/1973 | Calabrese et al. |
| 3,916,884 A | 11/1975 | Attenburrow |
| 3,916,885 A | 11/1975 | Gaylord, Jr. |
| 4,099,523 A | 7/1978 | Lowrey |
| 4,173,973 A | 11/1979 | Hendricks |
| 4,205,667 A | 6/1980 | Gaylord, Jr. |
| 4,325,363 A | 4/1982 | Berkeley |
| 4,401,111 A | 8/1983 | Blackstone |
| 4,413,619 A | 11/1983 | Garth |
| D278,747 S | 5/1985 | Peach, Jr |
| 4,520,801 A | 6/1985 | Lerman |
| 4,538,597 A | 9/1985 | Lerman |
| 4,562,833 A | 1/1986 | Pujals, Jr. |
| 4,582,051 A | 4/1986 | Greene et al. |
| 4,628,913 A | 12/1986 | Lerman |
| 4,643,174 A | 2/1987 | Horiuchi |
| 4,677,969 A | 7/1987 | Calabrese |
| 4,702,233 A | 10/1987 | Omicioli |
| 4,708,129 A | 11/1987 | Pujals, Jr. |
| 4,712,540 A | 12/1987 | Tucker et al. |
| 4,732,144 A | 3/1988 | Cunanan |
| 4,745,922 A | 5/1988 | Taylor |
| 4,827,915 A | 5/1989 | Gorsen |
| 4,854,306 A | 8/1989 | Pujals, Jr. |
| 4,886,052 A | 12/1989 | Calabrese |
| 4,940,043 A | 7/1990 | Burns et al. |
| 4,955,368 A | 9/1990 | Heimann |
| 4,987,891 A | 1/1991 | Gaylord, Jr. et al. |
| D314,623 S | 2/1991 | Calabrese et al. |
| 5,005,563 A | 4/1991 | Veale |
| 5,038,759 A | 8/1991 | Morgenstern |
| 5,058,572 A | 10/1991 | Schmid et al. |
| 5,060,637 A | 10/1991 | Schmid et al. |
| 5,097,824 A | 3/1992 | Garth |
| 5,156,588 A | 10/1992 | Marcune et al. |
| 5,180,361 A | 1/1993 | Moore et al. |
| 5,201,702 A | 4/1993 | Mars |
| 5,215,517 A | 6/1993 | Stevenson et al. |
| 5,230,698 A | 7/1993 | Garth |
| 5,275,581 A | 1/1994 | Bender |
| 5,302,170 A | 4/1994 | Tweardy |
| RE34,714 E | 8/1994 | Burns et al. |
| 5,346,461 A | 9/1994 | Heinz et al. |
| 5,366,438 A | 11/1994 | Martin, Sr. |
| 5,385,535 A | 1/1995 | McGuinness |
| 5,433,696 A | 7/1995 | Osti |
| 5,437,612 A | 8/1995 | Moore et al. |
| 5,437,617 A | 8/1995 | Heinz et al. |
| 5,445,602 A | 8/1995 | Grim et al. |
| D368,527 S | 4/1996 | Brooke |
| D369,660 S | 5/1996 | Myoga |
| 5,520,619 A | 5/1996 | Martin |
| RE35,290 E | 7/1996 | Druskoczi |
| 5,588,957 A | 12/1996 | Martin, Sr. |
| 5,593,382 A | 1/1997 | Rudy, Jr. et al. |
| 5,622,529 A | 4/1997 | Calabrese |
| 5,624,387 A | 4/1997 | McGuinness |
| D379,232 S | 5/1997 | Brooke |
| 5,632,722 A | 5/1997 | Tweardy et al. |
| 5,688,229 A | 11/1997 | Bauer |
| 5,716,335 A | 2/1998 | Iglesias et al. |
| 5,728,054 A | 3/1998 | Martin |
| D393,718 S | 4/1998 | Traut et al. |
| 5,785,670 A | 7/1998 | Hiebert |
| 5,788,658 A | 8/1998 | Islava |
| 5,795,315 A | 8/1998 | Traut et al. |
| 5,797,713 A | 8/1998 | Tweardy et al. |
| 5,797,863 A | 8/1998 | Kohnke |
| RE35,940 E | 10/1998 | Heinz et al. |
| 5,865,773 A | 2/1999 | Koledin |
| 5,904,662 A | 5/1999 | Myoga |
| 5,934,599 A | 8/1999 | Hammerslag |
| 5,964,722 A | 10/1999 | Goralnik et al. |
| 5,976,098 A | 11/1999 | Sereboff |
| 5,993,403 A | 11/1999 | Martin |
| 6,027,467 A | 2/2000 | Nakamura et al. |
| 6,036,664 A | 3/2000 | Martin, Sr et al. |
| D422,710 S | 4/2000 | Maynard |
| 6,045,522 A | 4/2000 | Grober |
| 6,045,523 A | 4/2000 | Donaldson |
| 6,050,965 A | 4/2000 | Pillai |
| 6,056,711 A | 5/2000 | Domamski et al. |
| 6,058,517 A | 5/2000 | Hartunian |
| RE36,745 E | 6/2000 | Rudy, Jr. et al. |
| 6,071,255 A | 6/2000 | Calabrese |
| 6,071,256 A | 6/2000 | Lam |
| 6,090,058 A | 7/2000 | Traut et al. |
| 6,165,146 A | 12/2000 | Giebeler |
| 6,183,501 B1 | 2/2001 | Latham |
| 6,202,953 B1 | 3/2001 | Hammerslag |
| 6,245,033 B1 | 6/2001 | Martin |
| 6,254,560 B1 | 7/2001 | Tweardy et al. |
| 6,308,345 B1 | 10/2001 | Williams, Jr. |
| 6,289,558 B1 | 11/2001 | Hammerslag |
| 6,315,746 B1 | 11/2001 | Garth et al. |
| 6,423,020 B1 | 7/2002 | Koledin |
| 6,458,090 B1 | 10/2002 | Walpin |
| 6,494,854 B1 | 12/2002 | Visness et al. |
| D475,139 S | 5/2003 | Myoga |
| 6,632,722 B2 | 10/2003 | Fujiwara et al. |
| 6,663,581 B1 | 12/2003 | Calabrese |
| 6,663,630 B2 | 12/2003 | Farley et al. |
| 6,726,643 B1 | 4/2004 | Martin |
| 6,733,469 B2 | 5/2004 | Miyaji et al. |
| 6,740,055 B2 | 5/2004 | Dominguez |
| 6,770,046 B2 | 8/2004 | Hansen |
| 6,872,188 B2 | 3/2005 | Caille et al. |
| 6,913,584 B2 | 7/2005 | Rudy, Jr. et al. |
| 6,921,376 B2 | 7/2005 | Tweardy et al. |
| 6,926,686 B2 | 8/2005 | Cheatham |
| 7,018,351 B1 | 3/2006 | Iglesias et al. |
| 7,041,073 B1 | 5/2006 | Patron |
| 7,070,573 B2 | 7/2006 | Axelsson |
| 7,090,652 B2 | 8/2006 | Santelli, Jr. |
| 7,090,653 B2 | 8/2006 | Moeller |
| 7,128,724 B2 | 10/2006 | Marsh |
| 7,141,031 B2 | 11/2006 | Garth et al. |
| 7,198,610 B2 | 4/2007 | Ingimundarson et al. |
| D542,919 S | 5/2007 | Leatt |
| 7,258,677 B2 | 8/2007 | Rudy, Jr. et al. |
| D552,742 S | 10/2007 | Leatt |
| 7,291,121 B2 | 11/2007 | Rudy, Jr. et al. |
| 7,297,127 B2 | 11/2007 | Lee et al. |
| 7,311,686 B1 | 12/2007 | Iglesias et al. |
| 7,371,221 B1 | 5/2008 | Baker |

(56) References Cited

U.S. PATENT DOCUMENTS

| | | |
|---|---|---|
| 7,371,222 B2 | 5/2008 | Heinz et al. |
| 7,399,288 B2 | 7/2008 | Chao |
| 7,442,176 B2 | 10/2008 | Cojbasic |
| D609,815 S | 2/2010 | Patterson |
| 7,674,234 B2 | 3/2010 | Calco et al. |
| D616,555 S | 5/2010 | Thorgilsdottir et al. |
| D616,996 S | 6/2010 | Thorgilsdottir et al. |
| D616,997 S | 6/2010 | Thorgilsdottir et al. |
| D617,907 S | 6/2010 | Waller |
| 7,815,585 B2 | 10/2010 | Vollbrecht |
| 7,846,117 B2 | 12/2010 | Leatt et al. |
| D631,167 S | 1/2011 | Leatt et al. |
| 7,878,995 B2 | 2/2011 | Harty |
| 7,896,827 B2 | 3/2011 | Ingimundarson et al. |
| 7,981,068 B2 | 7/2011 | Thorgilsdottir et al. |
| D643,978 S | 8/2011 | Abajo Alonso et al. |
| D644,331 S | 8/2011 | Sandhu |
| D644,332 S | 8/2011 | Sandhu |
| 7,992,261 B2 | 8/2011 | Hammerslag et al. |
| D647,623 S | 10/2011 | Thorgilsdottir et al. |
| D647,624 S | 10/2011 | Thorgilsdottir et al. |
| 8,038,635 B2 | 10/2011 | Dellanno |
| 8,038,636 B2 | 10/2011 | Thorgilsdottir et al. |
| D659,842 S | 5/2012 | Donaldson et al. |
| D662,597 S | 6/2012 | Chang |
| 8,216,167 B2 | 7/2012 | Garth et al. |
| D666,302 S | 8/2012 | Joseph |
| 8,257,292 B2 | 9/2012 | Linares |
| 8,545,423 B2 | 8/2013 | Patron |
| D692,568 S | 10/2013 | Chiang et al. |
| D693,014 S | 11/2013 | Chiang et al. |
| 8,679,044 B2 | 3/2014 | Thorgilsdottir et al. |
| 8,864,693 B2 | 10/2014 | Suarez et al. |
| 8,932,243 B2 | 1/2015 | Calabrese |
| 9,132,027 B2 | 9/2015 | Calco |
| D767,825 S | 9/2016 | Georgeson et al. |
| 9,668,906 B2 | 6/2017 | Thorgilsdottir et al. |
| 9,713,546 B2 | 7/2017 | Thorsteinsdottir et al. |
| 10,675,173 B2 | 6/2020 | Thorsteinsdottir et al. |
| 2002/0138028 A1 | 9/2002 | Rudy, Jr. et al. |
| 2002/0156408 A1 | 10/2002 | Cheatham |
| 2002/0156409 A1 | 10/2002 | Lee et al. |
| 2002/0169401 A1 | 11/2002 | Walpin |
| 2002/0173737 A1 | 11/2002 | Miyaji et al. |
| 2003/0055367 A1 | 3/2003 | Dominguez |
| 2003/0060744 A1 | 3/2003 | Caille et al. |
| 2003/0181838 A1 | 9/2003 | Garth |
| 2004/0039318 A1 | 2/2004 | Santelli, Jr. |
| 2005/0101896 A1 | 5/2005 | Calabrese |
| 2007/0027418 A1 | 2/2007 | Calco et al. |
| 2007/0073203 A1 | 3/2007 | Moenning et al. |
| 2007/0270728 A1 | 11/2007 | Chao |
| 2009/0247918 A1 | 10/2009 | Patron |
| 2010/0137768 A1 | 6/2010 | Thorgilsdottir et al. |
| 2010/0268139 A1 | 10/2010 | Garth |
| 2010/0298748 A1 | 11/2010 | Rosenfeld et al. |
| 2011/0034844 A1 | 2/2011 | Thorgilsdottir et al. |
| 2011/0066094 A1 | 3/2011 | Thorgilsdottir et al. |
| 2011/0224591 A1 | 9/2011 | Thorgilsdottir et al. |
| 2012/0053499 A1 | 3/2012 | Donaldson et al. |
| 2012/0130295 A1 | 5/2012 | Haider |
| 2012/0165712 A1 | 6/2012 | Calabrese |
| 2013/0060179 A1 | 3/2013 | Modglin |
| 2013/0281899 A1* | 10/2013 | Suarez ............... A61F 5/055 602/18 |
| 2013/0281900 A1 | 10/2013 | Suarez et al. |
| 2013/0310722 A1 | 11/2013 | Thorsteinsdottir et al. |
| 2014/0012172 A1 | 1/2014 | Calco |
| 2014/0107551 A1 | 4/2014 | Modglin |
| 2014/0323938 A1 | 10/2014 | Suarez et al. |
| 2015/0216708 A1 | 8/2015 | Garth et al. |
| 2016/0008158 A1* | 1/2016 | Martin ............... A61F 5/055 602/18 |
| 2016/0287424 A1 | 10/2016 | Webster et al. |
| 2017/0252198 A1 | 9/2017 | Thorsteinsdottir et al. |
| 2018/0078400 A1 | 3/2018 | Hsu et al. |
| 2018/0078401 A1 | 3/2018 | Hsu et al. |
| 2020/0281754 A1 | 9/2020 | Thorsteinsdottir et al. |

FOREIGN PATENT DOCUMENTS

| | | |
|---|---|---|
| CN | 201150587 Y | 11/2008 |
| CN | 201602923 U | 10/2010 |
| CN | 102227196 A | 10/2011 |
| CN | 202015274 U | 10/2011 |
| CN | 204655220 U | 9/2015 |
| CN | 105120808 A | 12/2015 |
| DE | 19547115 A1 | 6/1997 |
| DE | 19849302 A1 | 4/2000 |
| DE | 100 57 286 A1 | 5/2002 |
| EP | 1738724 A1 | 1/2007 |
| EP | 2653139 A1 | 10/2013 |
| EP | 2886088 A1 | 6/2015 |
| FR | 2 814 362 A1 | 3/2002 |
| GB | 2 165 157 A | 4/1986 |
| GB | 2 453 996 A | 4/2009 |
| JP | 2007-330808 A | 12/2007 |
| WO | 94/09728 A1 | 5/1994 |
| WO | 95/22304 A1 | 8/1995 |
| WO | 96/40018 A1 | 12/1996 |
| WO | 9843568 A1 | 10/1998 |
| WO | 2014102340 A1 | 7/2014 |

OTHER PUBLICATIONS

Levangie et al., "Joint Structure and Function: A Comprehensive Analysis", Fourth Edition, Chapter 4: The Vertebral Column, 2005 F.A. Davis Company, Philadelphia, PA, pp. 161-164.

Hsu et al., AAOS Atlas of Orthoses and Assistive Devices, Mosby, Elsevier Fourth Edition, 2008, Philadelphia, PA, p. 117-122.

Product Information Sheet, Philadelphia Tracheotomy Collar, obtained from www.ossur com, prior to Aug. 6, 2010, 1 page.

Product Information Sheet, Platazote Sheets, WBC Industries, obtained from www wbcindustries.com prior to Aug. 6, 2010, 2 pages.

"Range-of-Motion Restriction and Craniofacial Tissue-Interface Pressure From Four Cervical Collars", The Journal of Trauma Injury, Infection, and Critical Care, vol. 63, No. 5, Nov. 2007, pp. 1120-1126.

"Ossur Is Immobilization", www.ossur.com, 2008, pp. 1-16.

"Miami J Patient Care Handbook", www.ossur.com, 2010, pp. 1-16.

Jacobson et al. "Improving Practice Efforts to Reduce Occipital Pressure Ulcers", Journal of Nursing Care Quality, vol. 23, No. 3, 2008, pp. 283-288.

Bell et al. "Assessing Range of Motion to Evaluate the Adverse Effects of Ill-Fitting Cervical Orthoses", The Spine Journal, vol. 9, 2009, pp. 225-231.

Karason et al. "Evaluation of Clinical Efficacy and Safety of Cervical Trauma Collars: Differences in Immobilization, Effect on Jugular Venous Pressure and Patient Comfort", Scandinavian Journal of Trauma, Resuscitation and Emergency Medicine, 2014, pp. 1-7.

International Search Report from PCT Application No. PCT/US2017/019391, dated May 18, 2017.

Partial International Search Report from PCT Application No. PCT/US2017/050206, dated Dec. 5, 2017.

Product Brochure, "Capital Collar Enhanced," DeRoyal, 2014, 2 Pages.

Product Brochure, "Instructions for Use Eclipse Cervical Collar," VQ OrthoCare, 2015, 2 Pages.

Product Brochure, "Miami J Advanced By OSSUR," www.ossur.com, 2012, 4 Pages.

Product Brochure, "Miami J Cervical Collar," www.ossur.com, 1 Page.

Product Brochure, "Proglide Cervical Collar," OPTEC, www.optecusa.com, 1 Page.

Product Brochure, "Vista Upper Spine," Aspen Medical Products, 2015, 6 Pages.

* cited by examiner

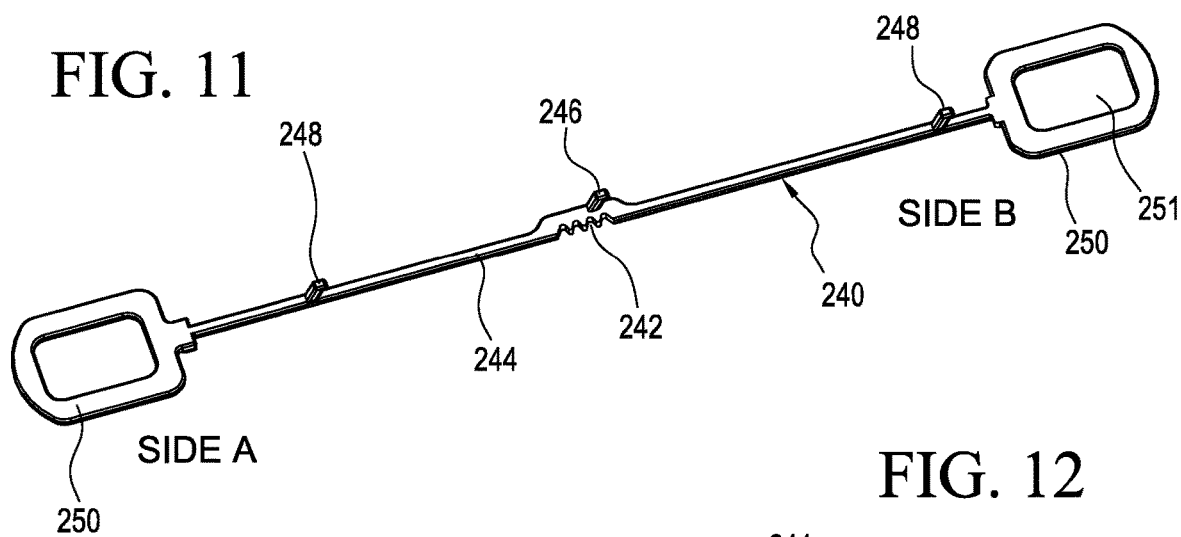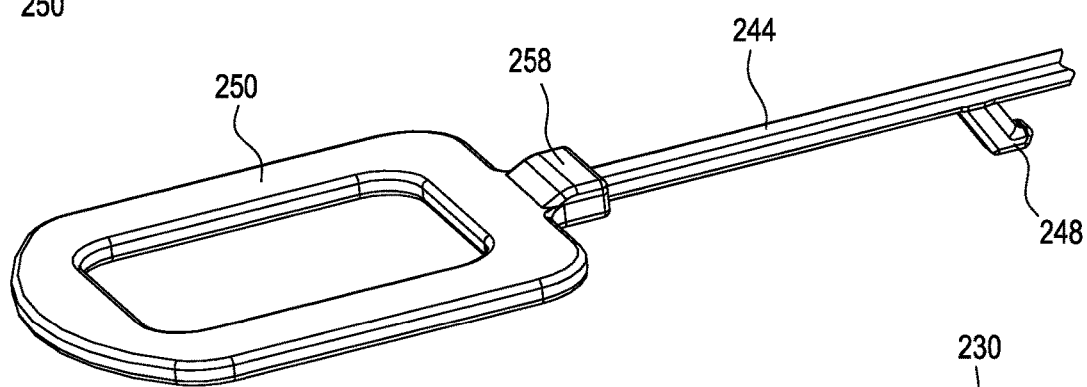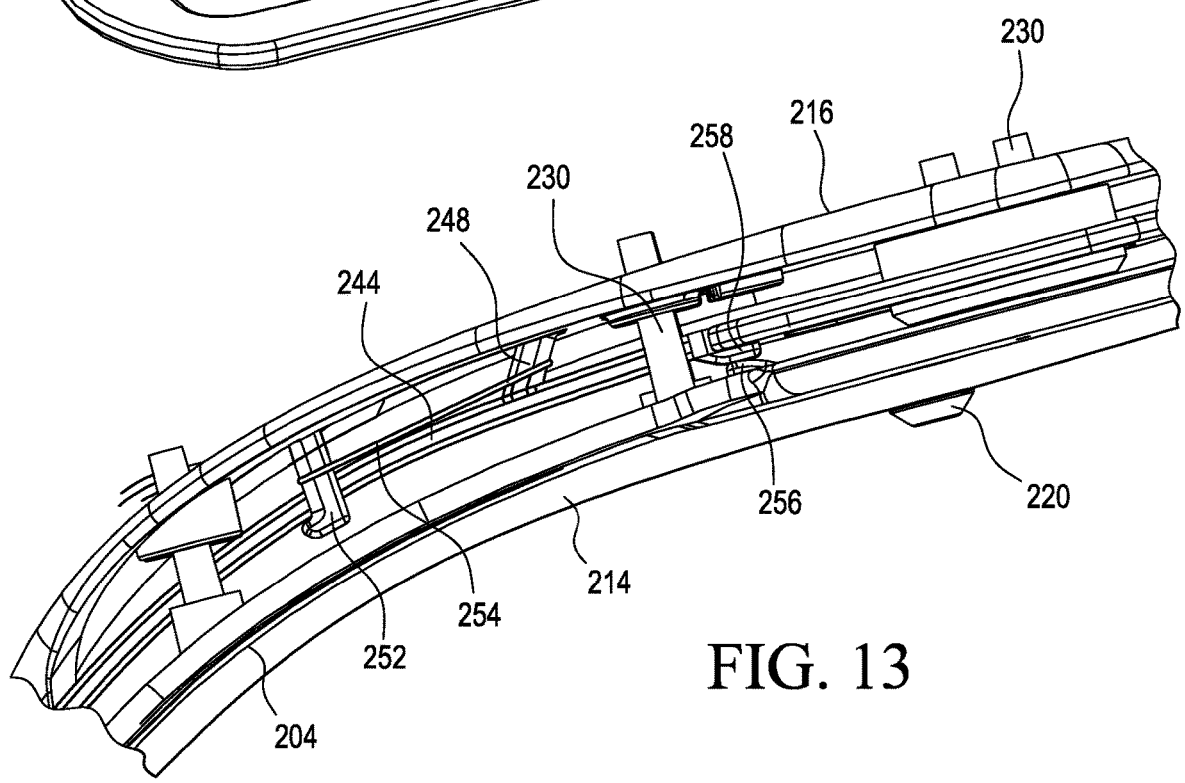

CERVICAL COLLAR HAVING HEIGHT ADJUSTMENT

CROSS-REFERENCE TO RELATED APPLICATIONS

This disclosure incorporates by reference U.S. Pat. No. 5,632,722, granted May 27, 1997, U.S. Pat. No. 6,254,560, granted Jul. 3, 2001, U.S. Pat. No. 7,981,068, granted Jul. 19, 2011, U.S. Pat. No. 8,038,636, granted Oct. 18, 2011, U.S. Pat. No. 8,679,044, granted Mar. 25, 2014, U.S. Pat. No. 9,713,546 granted on Jul. 25, 2017, and U.S. patent application publication no. 2016/0287424, published Oct. 6, 2016.

FIELD OF THE DISCLOSURE

The present disclosure relates to an orthopedic device, and more specifically to cervical collars having height adjustability at a front part, while providing a platform for securing known other components of a cervical collar thereto without modifying their anatomical contours and connection to the height adjusted components.

BACKGROUND

Cervical collars are used for treating conditions of the neck and the cervical spine by cervical spine immobilization. These collars may handle whiplash and other such injuries, where support for the head and neck of the patient is needed, and function to partially immobilize the head and neck of the patient and relieve spasm or strain to which the neck muscles of the patient might be subjected by transferring weight or force from the head of the patient to the shoulders or adjacent areas of the patient. Other collars may be arranged for complete or near complete immobilization of the head and neck of the patient to reduce risk of secondary damage to the spinal cord.

A challenge in designing a cervical collar is balancing desired immobilization with user comfort, such as venous pressure. Immobilization may be measured by five planes of movement, including flexion, extension, lateral tilt to right and left, and rotation of the neck to right and left, and is considered generally as cervical range of motion (CROM).

Unfortunately, many patients using cervical collars develop decubitus or decubitus ulcers (also known as bed sores, pressure sores, or trophic ulcers) when wearing cervical collars. These ailments, which involve a breakdown of tissue overlying a bone, arise when tissues overlying a bony prominence are subjected to prolonged pressure against an object such as a cervical collar. Besides affecting superficial tissues such as the skin, decubitus and decubitus ulcers also can affect muscle and bone. Restrictive collars are the root causes of skin breakdown in the trauma population. As pressure-ulcers are among the most common, yet serious and costly, complications of routine spinal immobilization, it is desirable to provide cervical collars that minimize the probability of ulcers.

Moisture and pressure are two major factors which contribute to the formation of decubitus. Once a decubitus ulcer forms, there is no good method of determining the extent of tissue damage. Once started, decubitus can continue to progress through the skin and fat tissue to muscle and eventually to bone, and is very difficult to treat and arrest. In extreme cases, surgical replacement of bone, muscle and skin are required to restore that portion of the body of the patient where decubitus has formed.

It is desirable to eliminate or at least minimize the effect of pressure points when using cervical collars. The likelihood of contracting decubitus can be greatly reduced by a more even distribution of pressure to several parts of the body of the patient.

Multiple studies have evaluated CROM and the likelihood of tissue-interface pressure (TIP) exerted by commercially-available cervical collars. One of the known commercial collars that has proven successful at striking the balance of minimal TIP and most restriction of CROM is the Miami J collar (Ossur, hf, Reykjavik, Iceland). Multiple studies have validated the features of the Miami J collar, including: Tescher, A. N. et al. Range-of-motion restriction and craniofacial tissue-interface pressure from four cervical collars. *Journal of Trauma-Injury Infection & Critical Care:* 2007; 63; 5; 1120-1126; Jacobson, T. M. et al. Efforts to reduce occipital pressure ulcers. *Journal of Nursing Care Quality;* 2008; 23; 3; 283-288; Karason, S. et al. Evaluation of clinical efficacy and safety of cervical trauma collars: differences in immobilization, effect on jugular pressure and patient comfort. *Scandinavian Journal of Trauma, Resuscitation and Emergency Medicine.* 2014. 22:37.

The Miami J collar is also described in U.S. Pat. No. 5,632,722, granted May 27, 1997; U.S. Pat. No. 6,254,560, granted Jul. 3, 2001; U.S. Pat. No. 6,921,376, granted Jul. 26, 2005. Variations of the Miami J collar, embodying the Miami J Advance collar, are described in U.S. Pat. No. 7,981,068, granted Jul. 19, 2011, and U.S. Pat. No. 8,679,044, granted Mar. 25, 2014.

A feature, preferably included in cervical collars to overcome limited adaptability to accommodate the body of the patient and the particular ailment prompting the need for wearing a cervical collar, is the facility for adjusting the relative positions of various components of the cervical collar. Part of the effectiveness of the Miami J collar is due to its ability for customization to different anatomical sizes of users.

As taught in U.S. Pat. No. 6,254,560, the Miami J collar has supports that enable customized pressure distribution and avoid skin breakdown. A front part of the Miami J collar has an adjustable upper support for the mandibular, chin and/or jaw of the user, and mounted to a lower support or sternum brace by means which permit relative movement between the upper support and the lower support. The posterior component or back part of the Miami J collar has an occipital support mounted to a back support by means which permit relative sliding movement between the occipital support and the back support. The shape of the upper support and occipital support are anatomically optimized for superior immobilization and patient comfort.

Both the upper support and the occipital support of the Miami J collar are uniquely anatomically shaped to maximize comfort and immobilization while minimizing pressure on the user. Because the upper support and the occipital support of the Miami J collar are clinically proven, it is desired that any improvements over the current Miami J collar provide means for preserving the function and shape of the upper support and occipital support of the current Miami J collar.

SUMMARY

The present disclosure describes an improved cervical collar for restricting head and neck movement to promote healing after an injury to the spinal column. The cervical collar has height, circumferential and angular adjustment to accommodate a wide variety of patient sizes and anatomical configurations, and to accommodate dimensional changes caused by increased or decreased swelling of the affected anatomical portions of the patients during treatment of the injury. The cervical collar is arranged to stabilize and immobilize the cervical area, by restricting lateral, sagittal and coronal movement, while improving comfort, and fit for individual patients.

Embodiments of the disclosure relate to a cervical collar having a height adjustment system between main and lower parts forming an anterior component, which permit the use of known upper and occipital supports in the cervical collar to maintain their functionality, comfort and fit, including their anatomical contours and connection to the height adjusted components. The height adjustment system is arranged for adjusting the chin height in a simple and effective manner that limits or mitigates tampering with the height while the collar is worn. The height adjustment system preferably includes using incremental height adjustment so the height may be locked at a desired height setting. The height adjustment system may be arranged to allow usage in existing collar designs, such as the Miami J or Miami J Advance collars, without substantially altering the shape and function of the mandibular and posterior component including an occipital support.

The height adjustment system mitigates or eliminates the need for pre-sizing methods, and is provided in a simplified manner to enable many height settings customizable for different users. The height adjustment system allows use of known upper and posterior components, which have been on the market for many years to serve many users of cervical collars, are clinically proven for their efficacy.

The height adjustment system allows for improved placement and configuration of a cervical collar on patients of different heights. The upper support and posterior component can be properly fitted against the chin and head of a patient by a clinician, followed by the extension of the anterior component against the patient's chest. Likewise the anterior component may be placed against the patient's chest and the upper support and posterior component can then be extended to the chin and head of the patient. The height setting can then be locked at the desired height setting by the clinician to ensure a proper fit for the user.

According to a general embodiment, a cervical collar has an anterior component arranged for connecting to a posterior component. The anterior component comprises a main support, and a lower support hingedly connected to the main support at first and second hinges. An elongate element or slidelock has first and second ends engaging the first and second hinges, such that the first and second ends are arranged for adjusting relative to the first and second hinges. A lock mechanism is configured for locking rotation of the lower support relative to the main support, and moving the elongate element between locked and unlocked conditions. The elongate element is biased into the locked condition, and may be configured to wedge parts of the hinged connection of the parts of the anterior component together in the locked condition.

In a method for adjusting an angle defined between the main support and the lower support, the method involves moving the elongate element relative to the main support and the lower support. A part of the main support is disengaged from a corresponding part of the elongate element to unlock the lower support from the main support. The lower support is moved relative to the main support. Once the lower support is placed at the desired angle relative to the main support, the part of the main support is engaged to the corresponding part of the elongate element to lock the lower support to the main support, which may be accomplish by wedging parts of the hinged connection together.

These and other features, aspects, and advantages of the present disclosure will become better understood regarding the following description, appended claims, and accompanying drawings.

BRIEF DESCRIPTION OF THE DRAWINGS

The drawing figures are not necessarily drawn to scale, but instead are drawn to provide a better understanding of the components thereof, and are not intended to be limiting in scope, but to provide exemplary illustrations. The figures illustrate exemplary configurations of an orthopedic device, and in no way limit the structures or configurations of a liner according to the present disclosure.

FIG. 11 is a perspective view of an embodiment of a slidelock in the cervical collar of FIG. 10 and showing a first side thereof.

FIG. 12 is a perspective detail view of the slidelock showing a second side thereof.

FIG. 13 is a perspective schematic view showing the slidelock of FIG. 11 in a portion of the cervical collar of FIG. 10.

DETAILED DESCRIPTION OF VARIOUS EMBODIMENTS

A. Introduction

Figure 1:
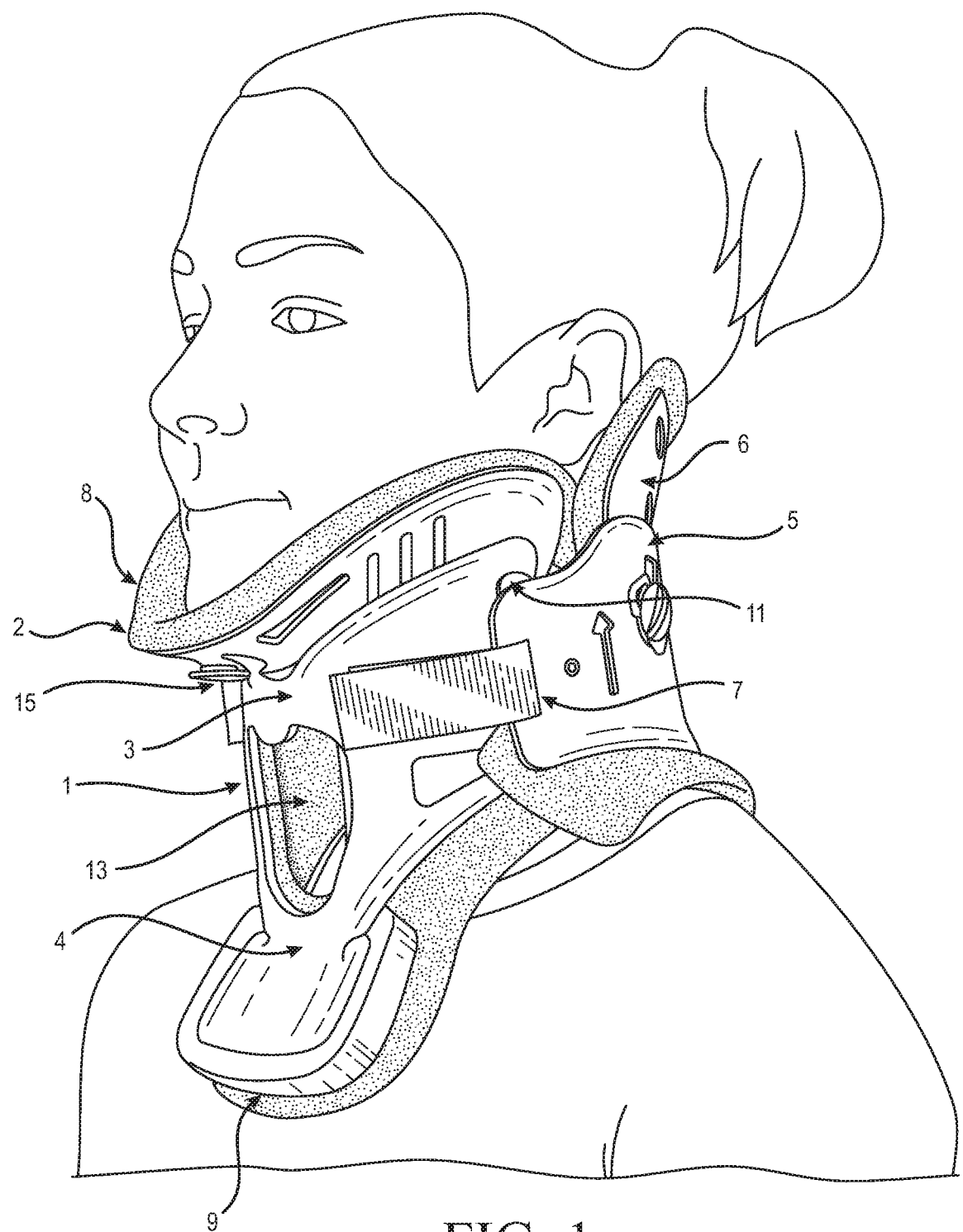
FIG. 1 is a perspective view of a known cervical collar under the commercial name Miami J.

Embodiments of an orthopedic device are provided for stabilizing and supporting anatomical portions of a wearer, for example, the neck and head of a wearer.

Although the embodiments of the disclosure are adapted for supporting and stabilizing anatomical portions of many wearers having various anatomical shapes and sizes, the embodiments of the disclosure may also be dimensioned to accommodate different types, shapes and sizes of anatomical portions.

A better understanding of different embodiments of the disclosure may be had from the following description read with the accompanying drawings in which like reference characters refer to like elements.

While the disclosure is susceptible to various modifications and alternative constructions, certain illustrative embodiments are in the drawings and are described below. It should be understood, however, there is no intention to limit the disclosure to the embodiments disclosed, but on the contrary, the intention covers all modifications, alternative constructions, combinations, and equivalents falling within the spirit and scope of the disclosure.

It will be understood that, unless a term is defined in this disclosure to possess a described meaning, there is no intent to limit the meaning of such term, either expressly or indirectly, beyond its plain or ordinary meaning.

While the foregoing embodiments have been described and shown, alternatives and modifications of these embodiments, such as those suggested by others may be made to fall within the scope of the invention. While the cervical collar has been described in combination with collar parts, it will be understood that the principles described may be extended to other types of orthopedic and prosthetic devices.

Reference characters are provided in the claims for explanatory purposes only and are not intended to limit the scope of the claims or restrict each claim limitation to the element in the drawings and identified by the reference character.

For ease of understanding the disclosed embodiments of an orthopedic device, the front or anterior, and rear or posterior portions of the orthopedic device are described independently. The anterior and posterior portions of the orthopedic device function together to form a supporting and stabilizing collar that encompasses the anatomical portions of the wearer.

The term "posterior" also has its ordinary meaning and refers to a location that is behind or to the rear of another location. Lastly, the term "anterior" has its ordinary meaning and refers to a location ahead of or to the front of another location.

The terms "rigid," "semi-rigid," "flexible," and "compressible" may be used herein to distinguish characteristics of portions of certain features of the orthopedic device. The term "rigid" should denote that an element of the device is generally devoid of flexibility. Within the context of support members or shells that are "rigid," it is intended to indicate that they do not lose their overall shape when force is applied, and they may break if bent with sufficient force. As for the term "semi-rigid," this term is used to connote properties of support members or shells that provide support and are free-standing; however such support members or shells may have some degree of flexibility or resiliency.

The term "flexible" should denote that features are capable of repeated bending such that the features may be bent into retained shapes or the features do not retain a general shape, but continuously deform when force is applied. The term "compressible" is used to qualify such structural features as being capable of being reduced in size or volume due to the exertion of force applied to the structural feature.

B. Components for Use with Following Embodiments

FIG. 1 exemplifies the known Miami J collar 1, as taught in the aforementioned patents and publications, particularly U.S. Pat. Nos. 5,632,722 and 6,254,560. The collar 1 includes an upper support 2 intended to support the mandibular, jaw or chin of the user that secures and/or rests upon an anterior component 3 of the collar. The upper support 2 is arranged for sliding movement with the anterior component 3 and for locking therewith by a side adjustment connection 11 and a central tab 15. The upper support 2 preferably has continuous padding 8 along a surface adjacent the user's jaw.

The anterior component 3 defines a sternum part 4, forming an extension adapted to extend below the clavicle of a user and adapted to rest against the sternum. The sternum part 4 carries a sternum pad 9 to avoid decubitus over long periods of wear of the collar. Besides the sternum pad 9, the anterior part 3 likewise includes padding along the surface facing the user.

The Miami J collar may be used by users with injuries other than those for which the cervical collar is most commonly used. The anterior component 3 forms an opening 13 which allows for access to the throat of the user, although because the anterior component is unitary and monolithic, the size of the opening 13 remains fixed.

The collar 1 includes a posterior component comprising lower and upper parts 5, 6, with the upper part serving as an occipital support. Both the lower and upper parts 5, 6 preferably include continuous padding, with the lower part intended to rest upon the back of the user, and the upper part intended to rest against the occiput of the head. The lower and upper parts 5, 6 are preferably attached for relative sliding movement between relative positions of the lower and upper parts to allow for different head sizes and proper and even pressure distribution across the body of the user.

Although not shown, the posterior component may be unitary and monolithic because it resembles the posterior component taught by U.S. Pat. No. 7,981,068 and found in the Miami J Advance collar. The posterior component is an anatomically configured 3D support contiguously formed with resilient or compliant edges. The support includes slots to provide ventilation and/or additional resilience or flexibility. The support portion also includes an anatomically shaped flared section shaped to correspond to and support an anatomical portion of a wearer, for example, the occipital region.

Both the upper support, and the anterior and posterior components are generally symmetrical about a vertical center line, and may be formed from rigid or semi-rigid plastic. The material forming the upper support, and the anterior and posterior components, may be flexible prior to donning the collar, but sufficiently rigid once the collar is donned to resist yielding due to weight exerted by the user.

A fastener 7 is used to secure the anterior and posterior components to one another. The fastener 7 comprises cooperating hook-and-loop attachments on the anterior and posterior components, with a strap bearing hook material extending from the posterior component and loop or hook receiving elements located on the anterior component.

Each of these embodiments is arranged to receive the upper support and posterior component of the Miami J collar, or the posterior component of the Miami J Advance collar in order to preserve the clinically recognized superior immobilization and comfort provided by the existing collars. It will be noted, however, that these embodiments are not restricted to only the upper support and posterior component of the Miami J and Miami J Advance collars, but can receive other upper support and posterior components of other known collars or those designed for each of the embodiments.

The height adjusted anterior component is arranged to preserve the anatomical contour and function of the known upper support and posterior component, despite the height adjustment of the anterior component and the tracheal opening thereof. The embodiments may have a varying height adjustment in that a center portion of the collar about the tracheal opening and generally along a vertical center line may increase greater in height than alongside portions of the anterior component proximate the connection to the posterior component. An example, although not limiting, is a 3:1 height difference at the center portion relative to the side portions.

While the embodiments may be associated with varying neck lengths among users, the sternal contour of users may likewise vary. The varying sternal contours of users may be resolved by positioning of the sternal contour, which may be achieved by adjusting the tracheal opening height or the height generally of the collar. While anatomical vertebral height and neck length plays a role in adjustment of the collar, the alignment of the spinal segments also has an effect in overall neck "length," i.e., a more kyphotic or flexed neck position "shortens" an otherwise anatomically longer or taller neck.

Another factor relating to the dimension of the cervical collar is the sternal contour. For instance, a very barrel chested individual (having a more horizontal sternal contour) may have the distal most dimension of the sternal extension of the brace contact considerably closer to the mandible than the patient with a very vertical sternum.

In all situations suggested above, mandible dimensions would be relatively the same, it is the orientation of the neck elements and its attachment to and the contour of the sternal segment that plays the largest role in overall collar height adjustment. The mechanism affording mandible and sternal height adjustment can accommodate the varying contours and dimensions.

C. Embodiments of the Cervical Collar

Figure 2A:
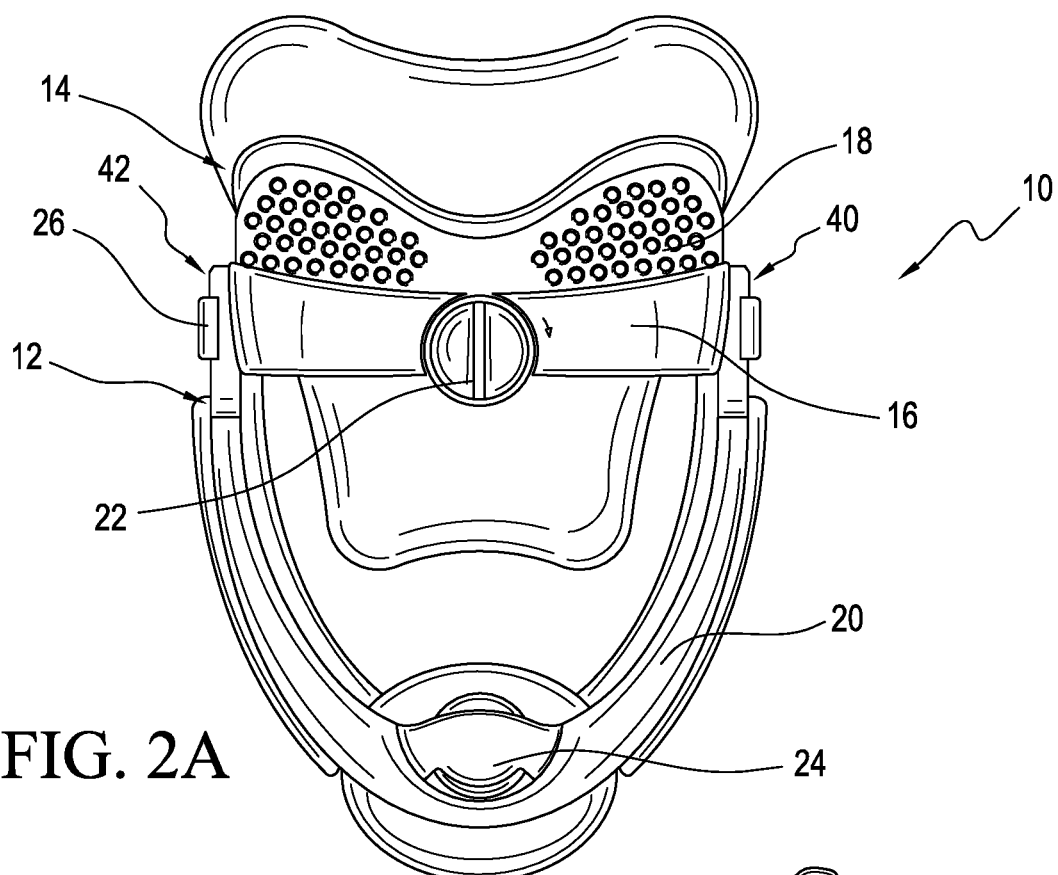
FIG. 2A is a frontal elevational view of a cervical collar.
Figure 2B:
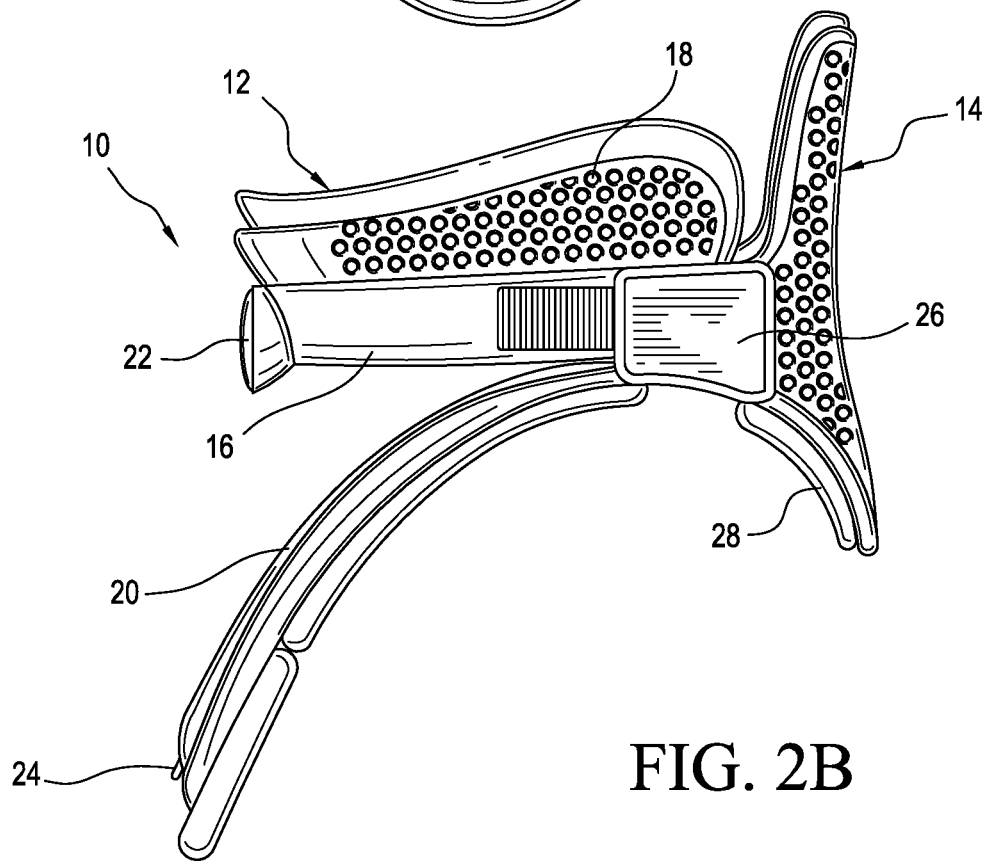
FIG. 2B is a side elevational view of an embodiment of a cervical collar of FIG. 2A.

According to the embodiment of FIGS. 2A and 2B, a cervical collar 10 has an anterior component 12 arranged for connecting to a posterior component 14. The posterior component 14 may be similarly arranged as the similar part in U.S. Pat. No. 7,981,068, as discussed above. The anterior component 12 comprises a main support 16, an upper support 18 arranged for being received by the main support 16, and a lower support 20 hingedly connected to the main support 16 at first and second hinges or end portions of the main and lower supports forming such hinges. In the depicted embodiments, the first and second hinges are formed by such end portions of the main and lower supports, and there are not separate hinges in addition to the end portions. However, the application is not limited to such arrangement, and additional components could be added to the end portions of the main and lower supports which could be considered as hinges in addition to the end portions of the main and lower supports.

A lock mechanism 22 is arranged for locking rotation of the lower support 20 relative to the main support 16, such that the hinges are locked according to different angular configurations of the lower support 20 relative to the main support 16. An adjustment mechanism 24 is located centrally along a lowermost portion of the lower support 20, and may be configured for adjustment relative to and away from a sternum of a user for improving comfort and fit of the cervical collar.

As evident from FIGS. 2A and 2B, the anterior component 12 preserves the general contours known in the Miami J collar, particularly the peripheral outline of the anterior component of both the main support 16 and lower support 20, which enables easy attachment to the known upper or upper support 18 and posterior component 14. Specifically, the upper support 18 may have a configuration that is the same as in U.S. patent application publication no. 2013/0310722, and U.S. Pat. No. 6,254,560. The profile of the upper support 18 is preferably taken from the Miami J collar, however other upper supports may be used and the embodiments are not limited to solely the Miami J collar profile.

Because the main and lower supports are adjustable relative to one another, the upper support is preferably maintained in a stationary relationship with the main support. However, the upper support is not necessarily rigid, but may flex according to the anatomy of the user, but become rigid or stable to movement once the collar is placed and tightened securely on the user.

Generally, when fitting a cervical collar having an anterior component 12, a clinician fits the upper support 18 and posterior component 14 against a patient's chin and head, arranged for the desired level of immobilization and support. The clinician then adjusts the lock mechanism 22 to secure the anterior component 12 against the chest and shoulders of the patient by articulating the lower support 20 relative to the main support 16. A clinician may also first fit the anterior component 12 against the patient's chest and then regulate the lock mechanism 22 to extend the main support 16 and posterior component 14 to the chin and head of the patient. The height setting is maintained by the lock mechanism 22 once released at the desired height setting to ensure a proper fit for the user.

Figure 6A:
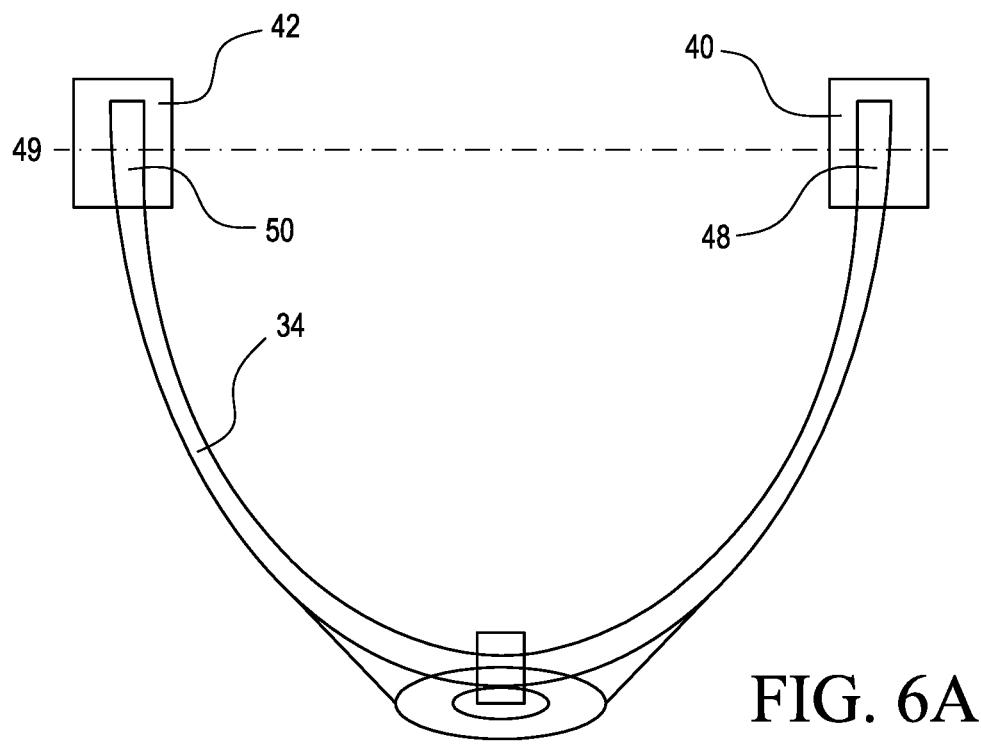
FIG. 6A is a schematic plan view of the elongate element in a locked condition.
Figure 6B:
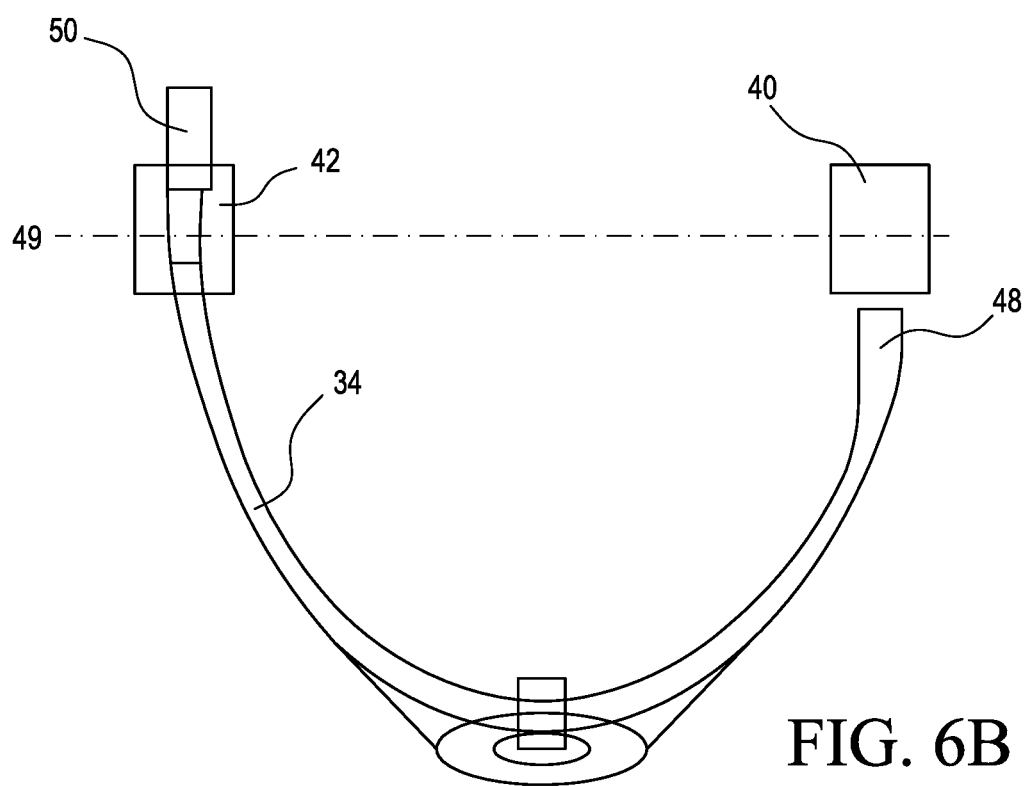
FIG. 6B is a schematic plan view of the elongate element in an unlocked condition.

Referring to FIGS. 6A and 6B, the first and second ends 48, 50 of an elongate element 34 or sliding lock or slidelock, as discussed periodically herein, are spatially located differently relative to the first and second hinges 40, 42 when in the unlocked condition. The first end 48 is axially offset from axis 49 from end portions 44, 46 of the main support and the lower support at the first hinge 40 in the unlocked condition. The end portions 44, 46 of the main and lower supports are generally coaxial relative to one another.

Figure 3A:
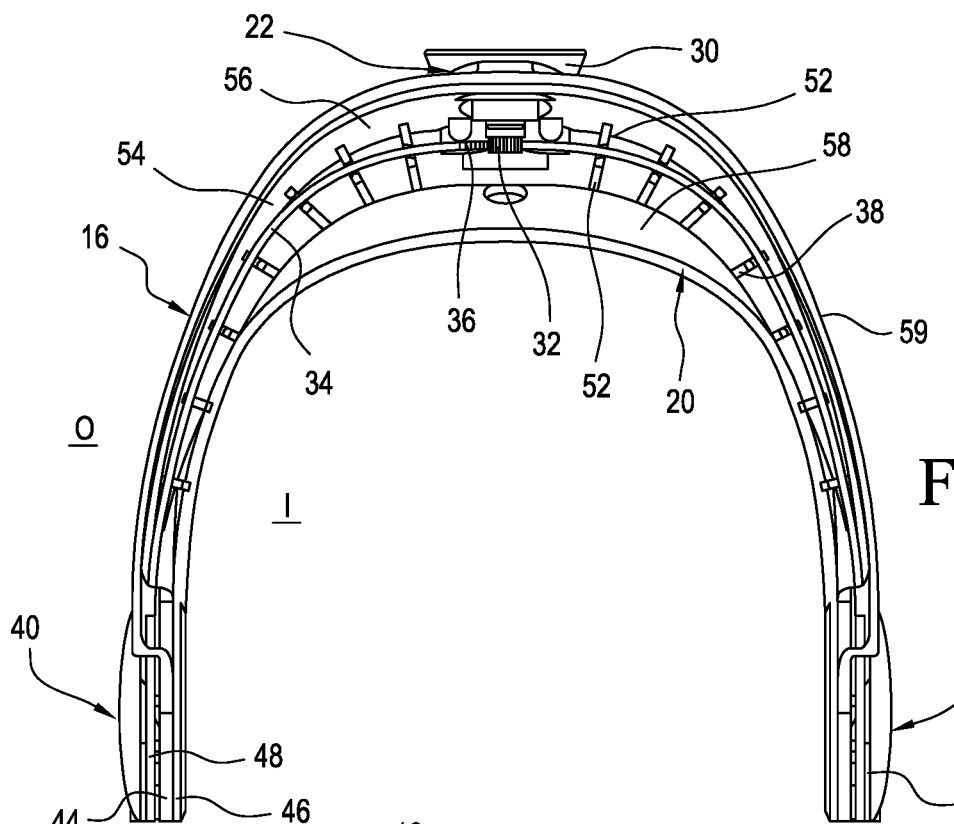
FIG. 3A is a top plan view of the main and lower supports of the cervical collar of FIG. 2A.
Figure 3B:
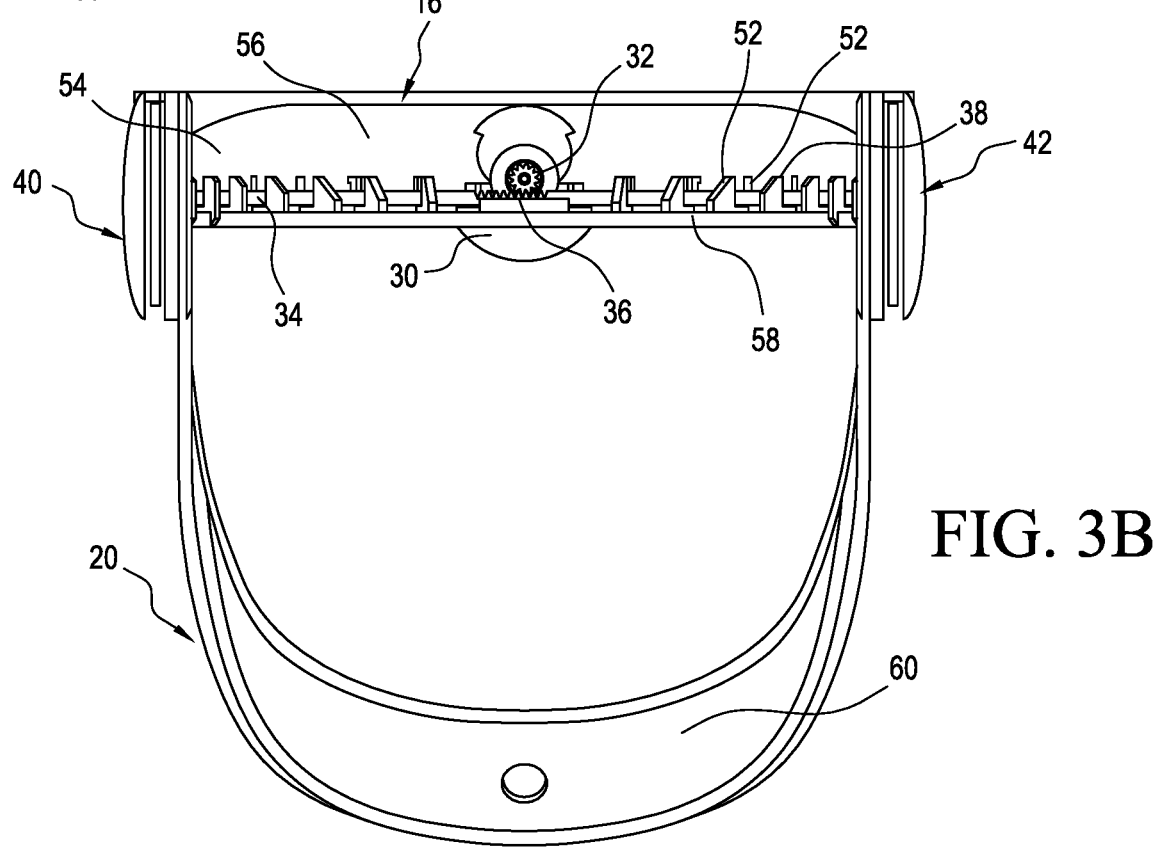
FIG. 3B is a rear elevational view of the main and lower supports of the cervical collar of FIG. 2A.
Figure 4:
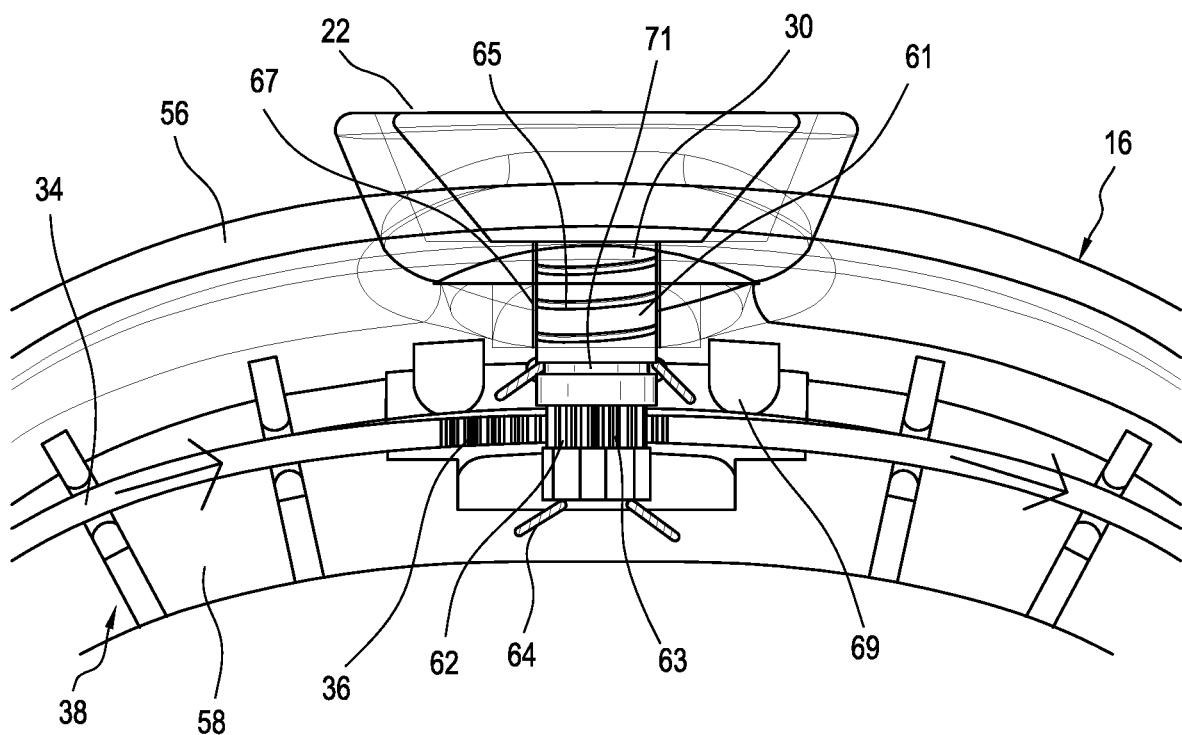
FIG. 4 is a detail plan view of the lock mechanism in FIG. 3A.

As illustrated in FIGS. 3A, 3B and 4, the elongate element 34 is slidably located within an arcuate guide 54 defined by the main support 16 along an inner side I thereof. The inner side I of the main support 16 defines a plurality of guides 38 for retaining the elongate element 34 within the arcuate guide 54. According to the illustrated embodiment, the guides 38 each define a post 52 having a height greater than a thickness of the guides 38. The arcuate guide is depicted as a tray but it may likewise be configured as a flange, boss, segmented protrusions, or other appropriate structure to route the elongate element of the main support or upper support.

The arcuate tray 54 is defined by a base portion 58 and an upper wall 56 of the main support 16. The base portion 58 extends outwardly from the upper wall 56 in a generally perpendicular orientation.

The main support 16 has a generally arcuate configuration 59 adapted to extend about the mandible of a user, and may be considered to possesses an elongated C- or U-shape. The lower support has a generally arcuate configuration 60 and is contoured for being adapted for securing against a sternum of a user.

The lock mechanism 22 includes an actuator or dial 30 for adjusting the lock mechanism 22 from locked to unlocked conditions. The lock mechanism 22 includes the elongate element 34 having first and second ends 48, 50 engaging the first and second hinges 40, 42. The first and second ends 48, 50 are arranged for being displaceable relative to the first and second hinges 40, 42 between locked and unlocked conditions of the lock mechanism 22.

The lock mechanism 22 preferably includes a pinion 32 and a rack segment 36, or geared rack segment 36, for adjusting position of the elongate element 34. The pinion 32 defines a shaft 61 extending between the outer and inner sides of the main support 16 and a pinion portion 62 at a first end of the shaft 61. The shaft 61 engages the actuator 30 on the outer side of the main support 16 at a second end of the shaft 61. The pinion portion 62 engages a rack segment 36 defined by the elongate element 34, whereby rotation of the shaft 61 urges the elongate element 34 to slide relative to the main support 16.

The pinion portion 62 is recessed relative to the shaft 61, such that the shaft 61 has a diameter greater than the pinion portion 62. The pinion portion 62 is arranged to maintain engagement with the rack segment 36 of the elongate element 34. An end portion 63 of the pinion on the inner side preferably has a diameter greater than the pinion portion 62. The pinion portion 62 is recessed relative to the shaft 61 and the end portion 63. The shaft 61 engages a periphery of an opening 67 of the main support 16 via a threaded engagement 65.

While a rack and pinion system is shown and described, other adjustment and engagement systems may be used in combination with the elongate element or slidelock. Such other adjustment and engagement systems may be rotary or linear in nature, such as a slider, for causing displacement of the elongate element relative to the main support.

In the embodiment of FIG. 4, the lock mechanism 22 includes a least one spring element 64 arranged for returning the shaft 61 to a locked condition after rotation of the shaft 61 to the unlocked condition of the first and second hinges 40, 42 and release of the actuator 30. The spring element 64 is a Belleville disc. The spring element 64 biases against a groove 71 formed by the shaft 61 and a bias element 69 of the main support 16. The return force from the elongate element 34 may drive the actuator into the locked condition.

Figure 5:
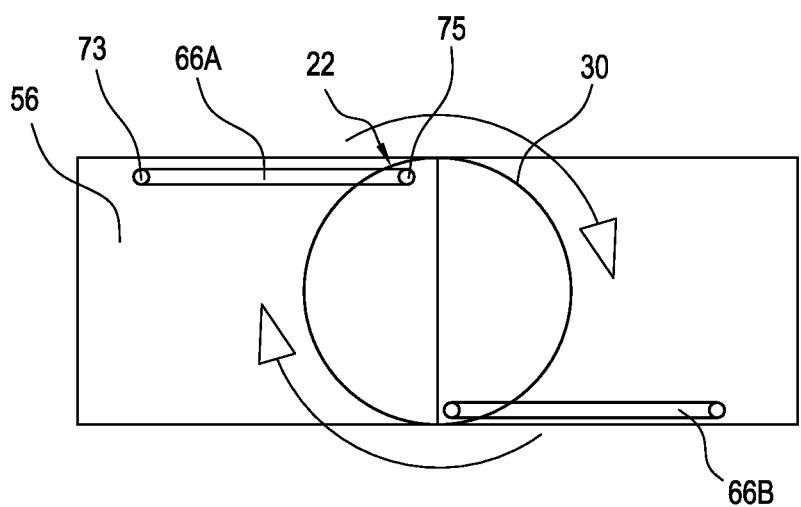
FIG. 5 is a schematic view of a variation of the lock mechanism of FIG. 3A.

According to the schematic representation in FIG. 5, the lock mechanism 22 has at least one elastic element 66A, 66B secured at a first end to a first retainer 73 on the main support 16 and a second retainer 75 on the lock mechanism 22, whereupon release of the lock mechanism, the at least one elastic element 66A, 66B urges the lock mechanism to a predetermined configuration. The actuator 30 may be resiliently or spring biased, such that it may be activated under force to an unlocked condition whereby such force returns the actuator to a predetermined locked condition; for example by merely releasing the actuator.

Figure 7A:
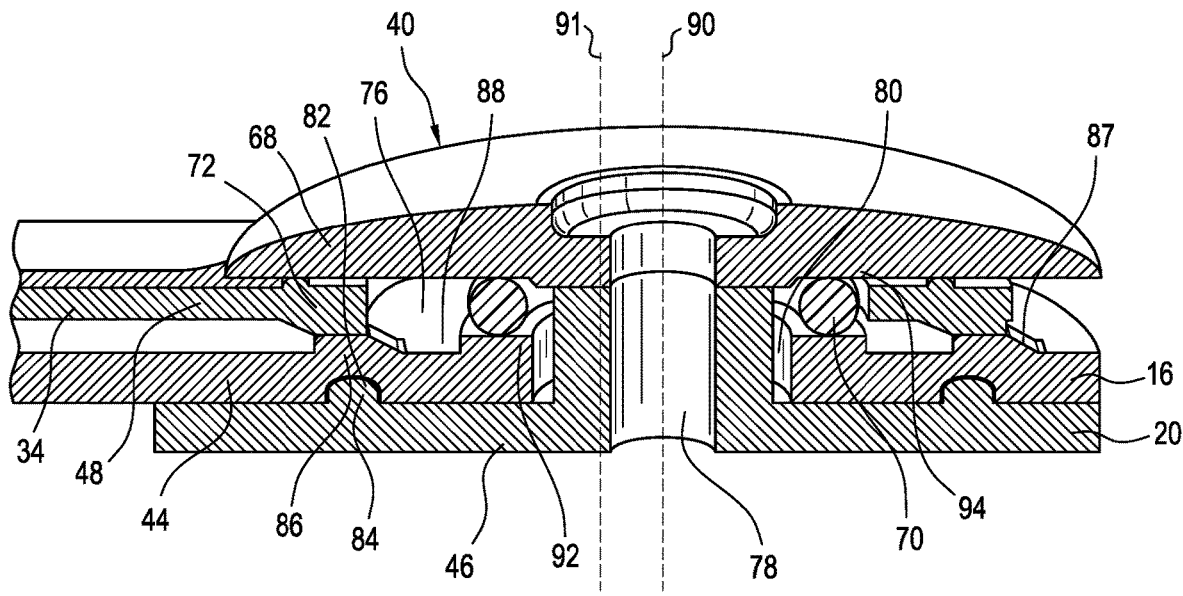
FIG. 7A is a schematic perspective view of the first hinge in a locked condition.
Figure 7B:
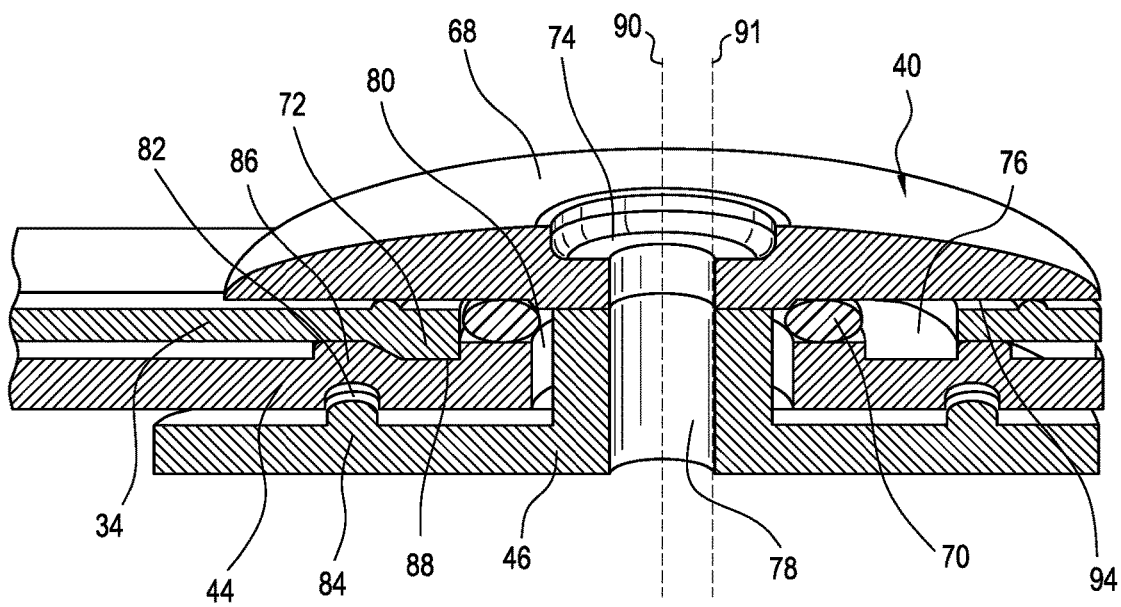
FIG. 7B is a schematic perspective view of the first hinge in an unlocked condition.

Referring to the depiction in FIGS. 7A and 7B, the first hinge or end portion 40 includes end portions 44, 46 of the main support and the lower support 16, 20, respectively, and a hinge cover 68 defining a hole 74. The end portions 44, 46 each define holes 78, 80 that are coaxial about a first axis 90 to one another and about which the first hinge or end portion 40 pivots. The first end 48 of the elongate element 34 is arranged to slidably adjust relative to the end portions 44, 46. The first end 48 defines an opening 76 axially offset from the first axis 90 and defined along a second axis 91 variable in location depending on the configuration of the lock mechanism 22.

The first end 48 of the elongate element 34 defines a detent projection 72 arranged to engage a ridge 86 defined by the end portion 44 of the main support. The end portion 44 defines a ramp 87 leading to the ridge 86 from a recess 88 defined by the end portion 44. The detent projection 72 is arranged to be received by the recess 88 and slide along the ramp 87 to the ridge 86 between locked and unlocked conditions of the lock mechanism 22. The ridge 86, the ramp 87 and the recess 88 are generally concentric with the first axis and the hole 78 of the main support 16.

A spring element 70, such as an O-ring, is concentrically disposed about the hole 78 of the main support and biased between a shoulder 92 defined by the main support 16 and an inner surface 94 of the cover 68. As shown in FIG. 7A, when the spring 70 is in an expanded configuration, it wedges the inner surface 94 of the cover 68 and the shoulder 92 together.

The end portion 46 of the lower support 20 defines a protrusion or detent 84 arranged to be received by a notch 82 defined by the end portion 44 of the main support. The detent 84 is received by the notch 82 in the locked condition of the main support and the lower support. The detent 84 is generally arranged concentrically with the hole 80 of the main support. As shown in FIG. 7A, in the locked condition, vertical interference prevents movement of the hinge. FIG. 7B shows how in the unlocked condition the spring element is compressed, and the detent may move.

Figure 8A:
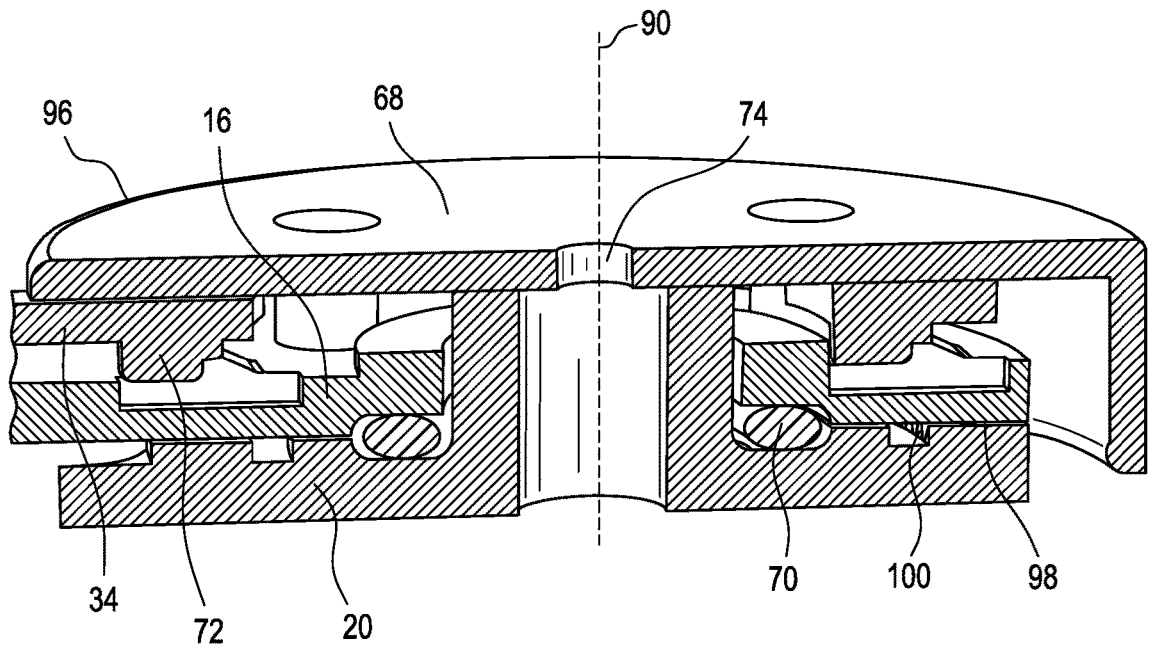
FIG. 8A is a schematic perspective view of a variation of the first hinge in a locked condition.
Figure 8B:
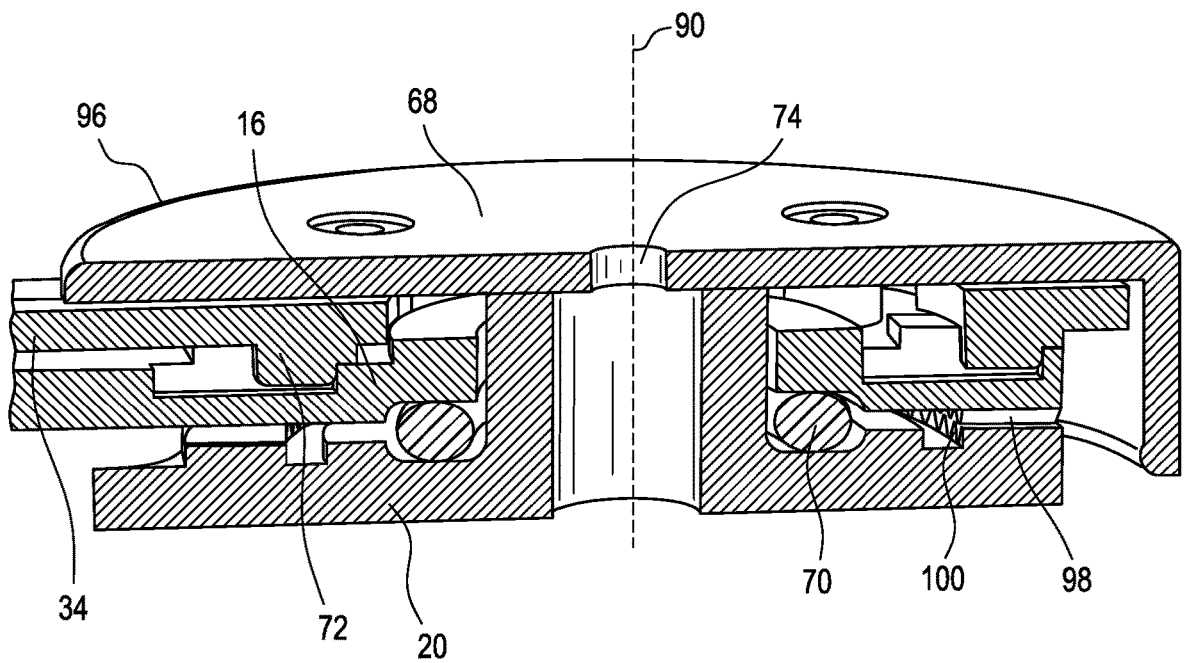
FIG. 8B is a schematic perspective view of the first hinge of FIG. 8A in an unlocked condition.

FIGS. 8A and 8B exemplify a variation of the hinge 96, whereby the main support and the lower support define a plurality of cooperating teeth 98, 100 engageable when the lock mechanism is in the locked condition, and disengaged from one another when the lock mechanism is in an unlocked condition.

Figure 9A:
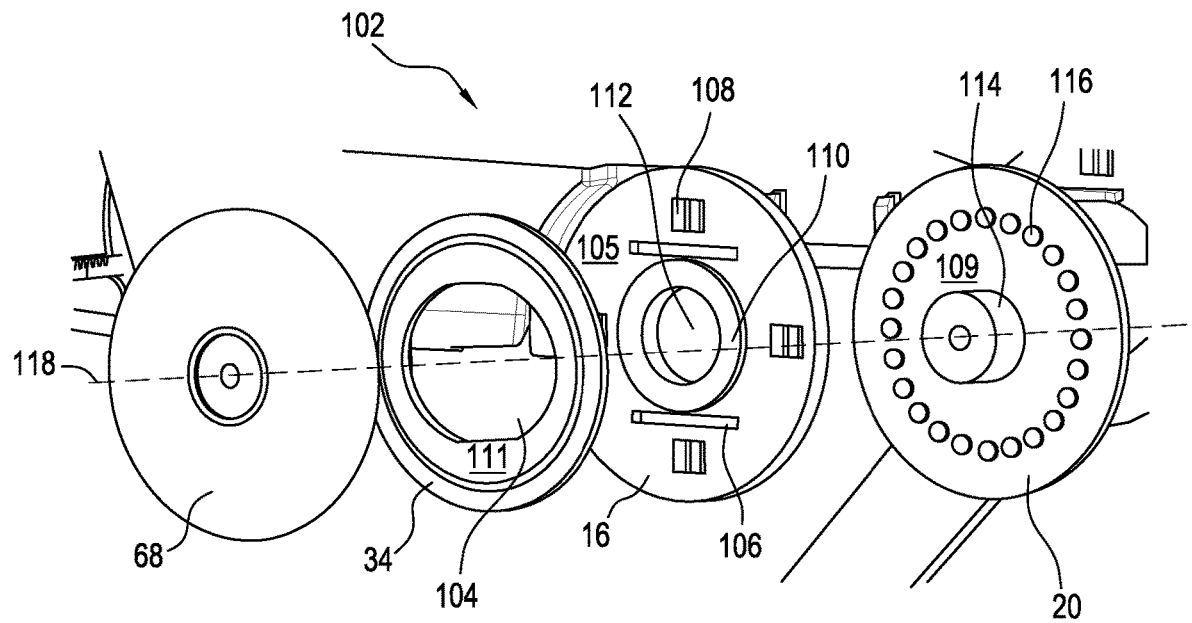
FIG. 9A is an outer exploded perspective view of another variation of the first hinge.
Figure 9B:
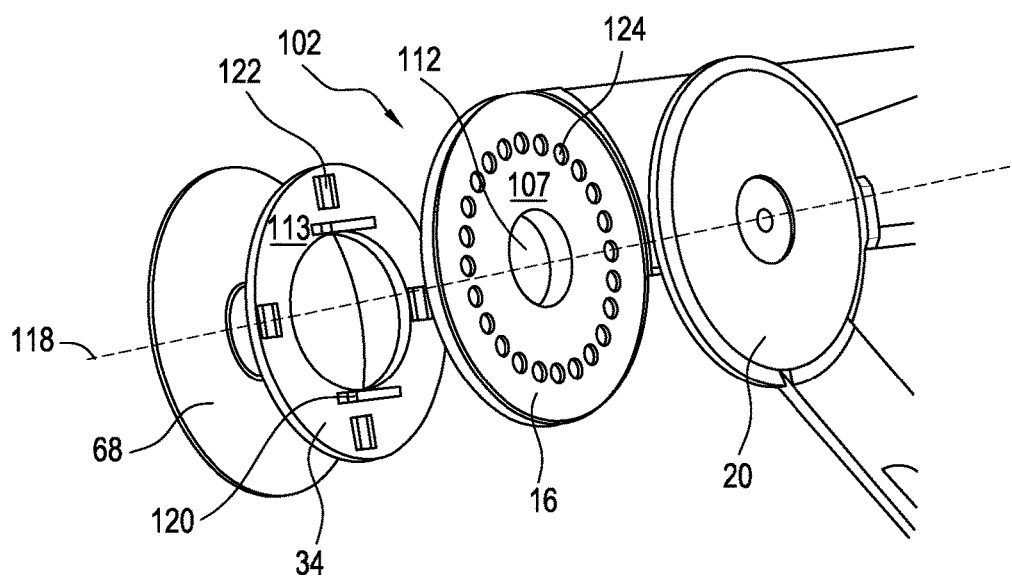
FIG. 9B is an inner exploded perspective view of the first hinge of FIG. 9A.

FIGS. 9A and 9B illustrate another embodiment of the hinge 102 wherein the end portion of the elongate element 34 defines an opening 104 and the main support 16 defines an opening 112 through which a post 114 of the lower support 20 extends to secure to the cover 68. Such a construction is similar to the embodiments of FIGS. 7A-8B. The opening 112 and the post 114 are coaxial along axis 118. The opening 104 of the elongate element 34 has an oblong profile arranged for being axially offset relative to the axis 118, and a first surface 111 is arranged for abutting the hinge cover 68.

The elongate element 34 defines at least one elongate bar 120 protruding from a second surface 113 thereof and is arranged for being received by a corresponding elongate recess 106 formed by the main support 16. The main support 16 defines a plurality of circumferentially spaced recesses 108 arranged for receiving at least one detent 122 formed by the elongate element 34. The main support 16 defines an annular shoulder 110 from a first surface 105 thereof and defined about the opening 112.

The main support 16 defines a plurality of receptacles 124 circumferentially spaced about the opening 112 along a second surface 107 thereof. The lower support 20 defines a plurality of circumferentially spaced bosses 116 along a first surface 109 thereof, arranged for being received by the receptacles 124.

Figure 10:
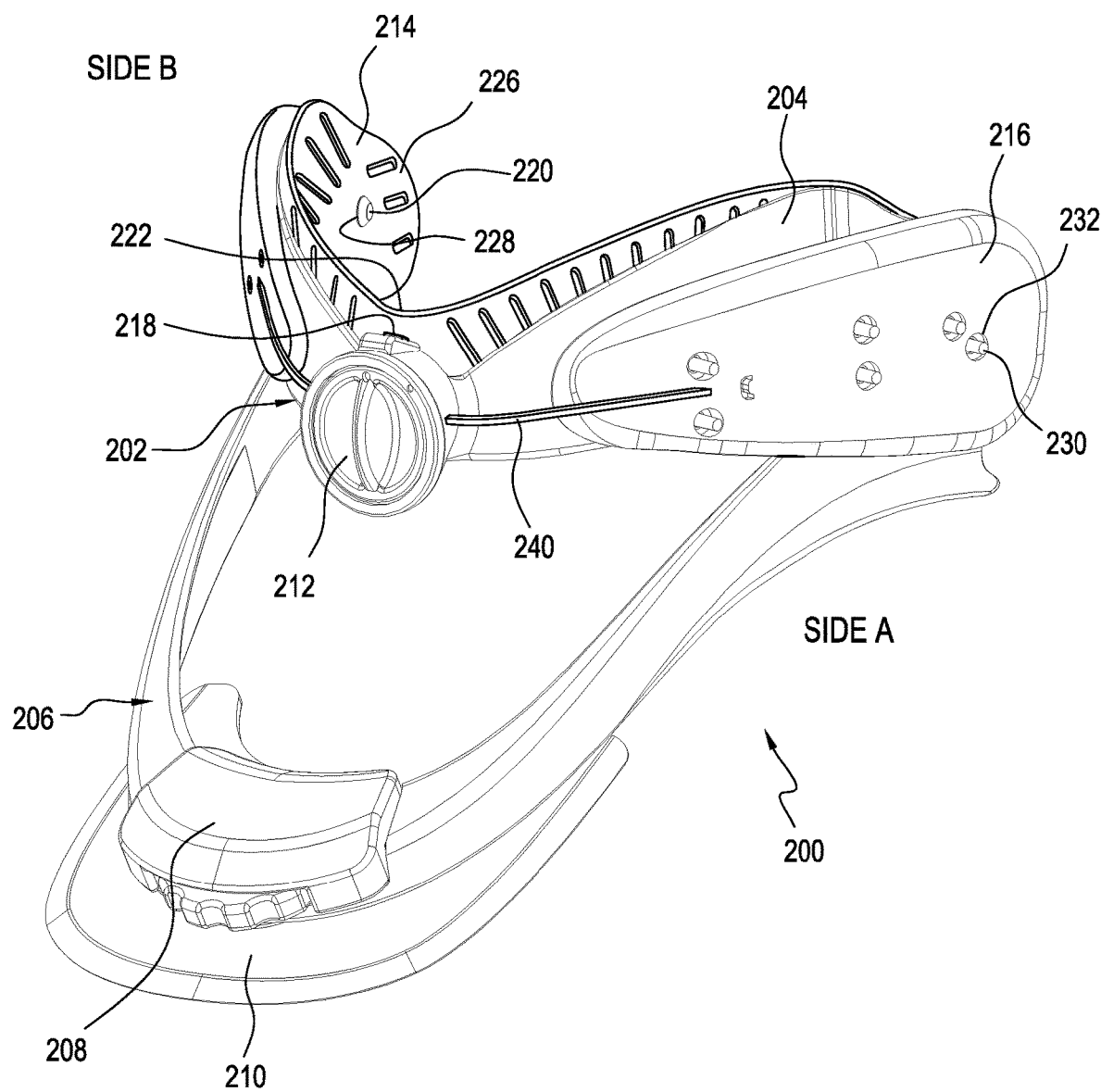
FIG. 10 is a perspective view of another embodiment of a cervical collar.

FIG. 10 exemplifies another embodiment of an anterior support 202 for a cervical collar 200 having a height adjustment system while preserving the contour 222 of the upper support 214 generally from the Miami J collar. The upper support 214, however, has improvements for securing to the main support 204 and features for increasing lateral immobilization.

The upper support 214 is arranged for easy attachment to the main support 204 by providing snap connections. A central portion at the front section of the main support 204 may have boss snaps 218 that fit and interlock with a corresponding aperture defined by the main support 204. Rear portions of the upper support 214 may define apertures corresponding to fasteners 220 formed by the main support 204 that engage the upper support 214, and aid in maintaining the upper support 214 in a desirable contour. The ability to easily attach an upper support to the main support enables a clinician to use differently-sized upper supports according to the user's anatomy. The upper and main supports may define apertures arranged for receiving fasteners not formed by either support, but are separate elements for securing the upper and main supports together.

The upper support 214 defines lateral extensions 226 on opposed sides thereof which are oriented to extend away from the central portion of the upper support, and effectively lengthen the extent the upper support extends along a user's mandibles. The lateral extensions are found to aid in increasing lateral immobilization of a user when wearing the collar.

The anterior support 202 includes a lower support 206 hingedly connected to the main support 204, and the locking and unlocking of the hinge is obtained by a lock mechanism 212 that may be similar to any of the aforementioned embodiments. A lower or sternum pad 210 is attached to a lower or lowermost portion of the lower support 206. The lower support 206 may include an adjustment mechanism 208 for adjusting pressures and/or height of the lower pad 210 relative to the user's sternum.

Anterior support 202 has a cover 216 at the rearwardly portions, in contrast to the centrally located lock mechanism 212. The cover 216 generally covers the hinge connection between the main support 204 and the lower support 206, and further serves form part of the hinge connection. Specifically, the cover 216, forms a plurality of openings 232 through which posts 230 extend from the main support 204.

FIG. 11 depicts an embodiment of an elongate element or slidelock 240 useable in the hinge connection of the collar 200. The slidelock 240 defines a central rack 242 of teeth arranged to correspond and operatively engage elements forming part of the lock mechanism for enabling linear translation of the slidelock 240 relative to the main support, such as in the embodiment of FIGS. 3A-4. The elements of the lock mechanism may be similar to the pinion of FIG. 4, or may be a linear rack of teeth, or any other suitable feature or mechanism for engaging the central rack 242.

In this embodiment, as shown in FIG. 10, the slidelock 240 preferably slides over an outer surface of the main support 204 to cooperate with the main support 204 to arrest or prevent rotation of the lower support 206 relative to the main support 204. The main support 204 and the cover 216, as shown below, operate to guide the linear movement of the slidelock. The linear movement of the slidelock is intended relative to a rear portion of main support within such discrete section, while acknowledging that the slidelock is bendable about the arcuate contour of the main support while traveling between opposed directions, as better depicted referring to FIG. 3A.

The slidelock 240 defines elongate segments 244 extending from opposed sides of the central rack 242 to paddles 250 located at end portions for forming part of the hinge connection. The paddles 250 generally corresponding in proximate location to the end portion 257 of the lower support 206, to stabilize the end portion 257 in both the locked and unlocked conditions. An opening 251 defined by the paddles 250 is arranged so the paddle 250 corresponds to the end portion 257 in both locked and unlocked conditions, whereby it is within the periphery of the end portion 257, as exemplified in FIG. 15B. The slidelock 240 forms hooks 246, 248 along the elongate segments 244 preferably extending from a first surface of the slidelock that are engageable with elastic elements, as discussed more in connection with FIG. 13.

Referring to FIG. 12, the slidelock 240 preferably defines ramp 258 intended to be on Side A of the collar (and ramp 268 intended to be on Side B of the collar in FIG. 14B) preferably extending from a second surface of the slidelock 240 where the elongate segments 244 meet the paddles 250. It is within this area where the travel of the slidelock is intended as traveling linearly. According to the depicted embodiment, the ramp 258 on Side A of the collar generally decreases in height from the paddle 250 toward the central rack 242 and from the second surface of the slidelock 240.

Figure 14A:
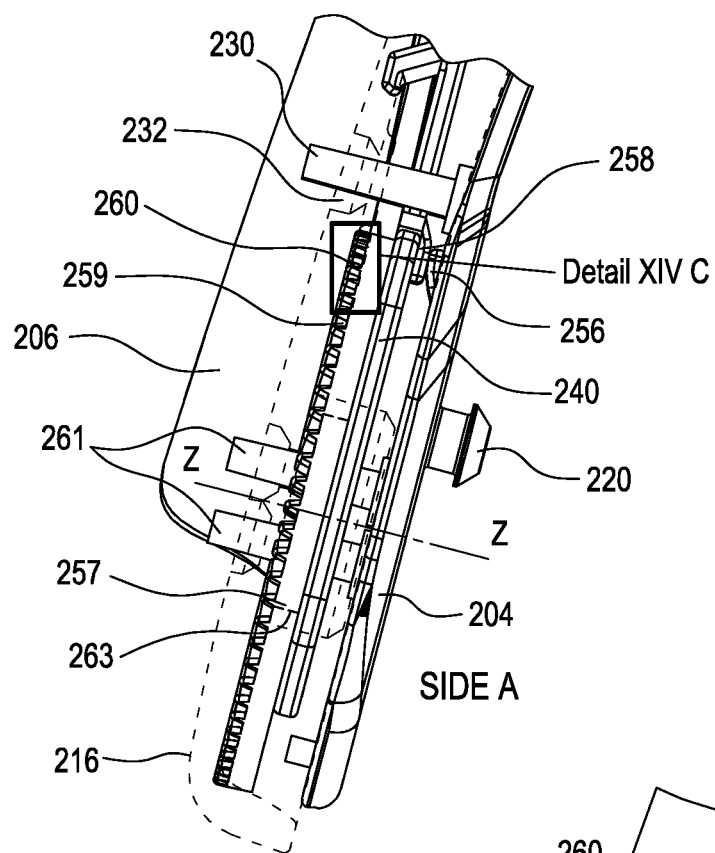
FIG. 14A is a perspective schematic view showing the slidelock of FIG. 11 in an end portion of side A of the cervical collar of FIG. 10 in a locked condition.
Figure 14B:
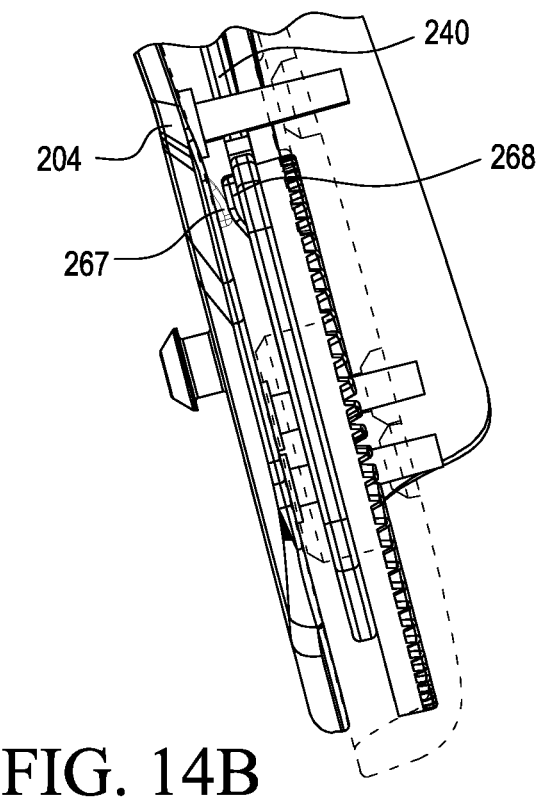
FIG. 14B is a perspective schematic view showing the slidelock of FIG. 11 in an end portion of side B of the cervical collar of FIG. 10 in an unlocked condition.

Referring to FIG. 14B, the ramp 268 on Side B of the collar generally increases in height from the paddle 250 toward the central rack 242 and from the second surface of the slidelock 240. In this manner, the ramps 258, 268 have oppositely oriented configurations to accommodate linear movement of the slidelock between locked and unlocked conditions so both Sides A, B undergo simultaneously the same locking or unlocking. The ramps 256, 267 have opposite orientations as the ramps 258, 268. Both ramps 258, 268 disengage at the same time from the corresponding ramps 256, 267 of the main support 204 in the unlocked condition, and engage at the same time with the corresponding ramps 256, 267 in the locked condition.

FIGS. 13 and 14A depict how the slidelock 240 operates relative to other components of the anterior component 202. Specifically, the slidelock 240 is slidably held by the main support 204, similarly as in the embodiment of FIGS. 3A-4, and may be likewise contained by the cover 216. The main support 204 defines a ramp 256 protruding from an outer surface and configured for engagement with the ramp 258 of the slidelock 240, which urges at least one engaging element 259 defined by a rear portion of the lower support 206 to engage at one engaging element 260 formed by the cover 216. The ramps 256, 258 effectively wedge the at least one engaging elements 259, 260 against one another to lock the hinge connection.

Figure 14C:
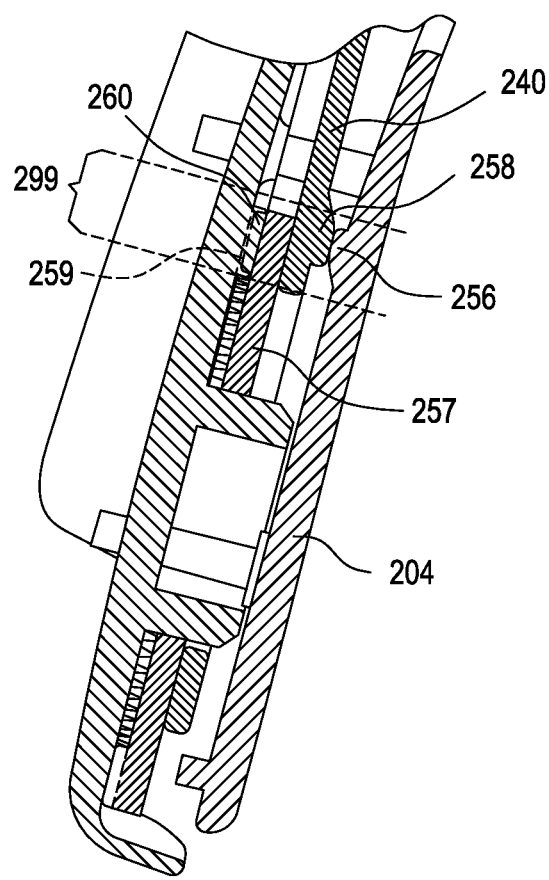
FIG. 14C is a detail cross-sectional view XIV C of FIG. 14A showing engagement of features in a locked condition of the collar of FIG. 10.
Figure 15A:
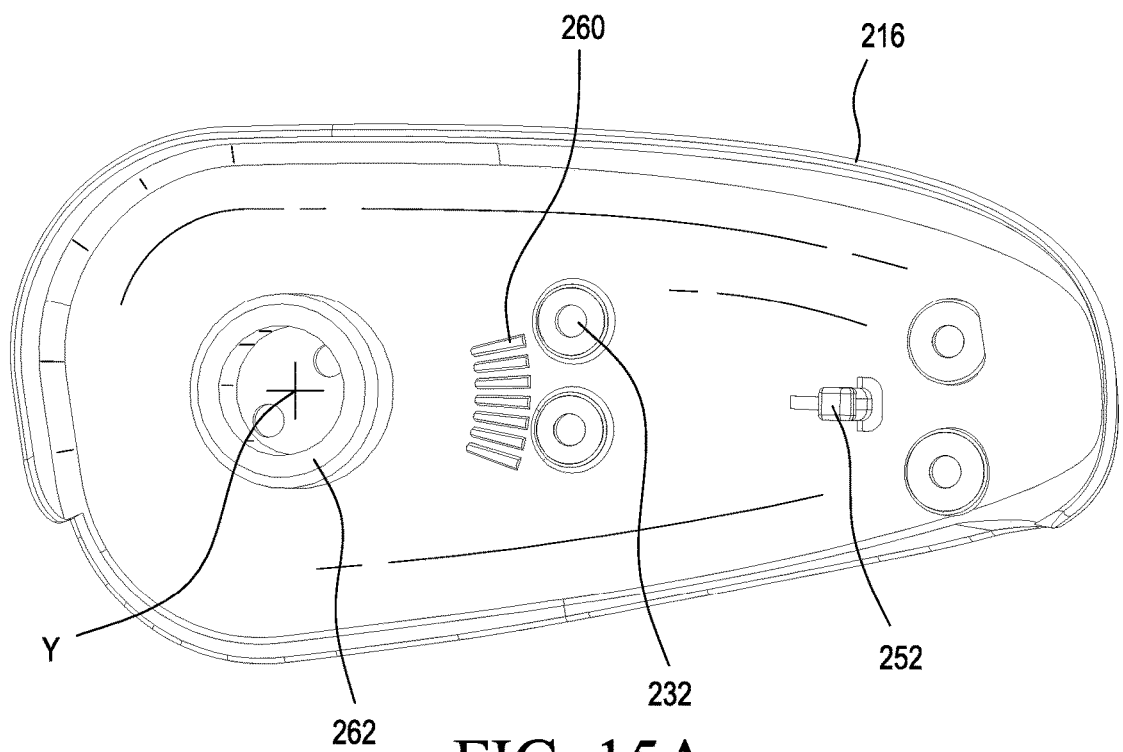
FIG. 15A is a perspective view of an inside surface of a side cover in the cervical collar of FIG. 10.

According to the depicted example of FIGS. 14 and 15A, the end portion 257 of the lower support has a disk shape, and rotates about an axis Z-Z of the disk shape relative to a circular boss 262 of the cover 216. The end portion 257 may have a central opening 263 coaxial with the axis Z-Z, which engages the boss 262 and is coaxial with an axis Y-Y of the boss 262. The main support 204 has at least one post 261 extending through the opening 263 and through one of the openings 232 of the cover 216 for providing stability to rotation of the end portion 257. As the ramps 256, 258 engage and disengage, the end portion 257 axially moves relative to the at least one post 261, and the boss 262 has a sufficient height to maintain the engagement of the end portion 257 in both the locked and unlocked conditions. The cooperation of the ramps, and regulation thereof by the slidelock, control the height clearance in the hinge and the freedom of the disengagement of the lower support from the main support and/or cover.

As shown in FIGS. 14A and 15A, the at least one engaging elements 259, 260 are teeth adapted to engage one another in a locked condition of the collar 200. For simplicity, the cover 216 is shown transparently. The at least one engaging element 259 of the lower support 206 forms teeth that extend laterally from the disk shape or parallel to the axis Z-Z of the end portion 257. Preferably, the teeth extend laterally relative to the circumference of the end portion 257, and may extend completely or partially about the circumference. The at least one engaging element 260 of the cover 216 may be teeth oriented arcuately to smoothly engage the teeth of the at least one engaging element 259 of the lower support 206.

FIG. 14C shows how the ramps 256, 258 (for both Sides A and B) fall generally within a range of the at least one engaging elements 259, 260 to form an engagement zone 299 when the collar is in a locked condition. According to the engagement zone, the ramps 256, 258 wedge against one another, and are generally juxtaposed or stacked-up coinciding over the at least one engaging elements 259, 260 to urge them to mesh together to assure secure locking of the main support to the lower support, and hence the cervical collar in a selective angulation. According to the unlocked condition (not shown), the ramp 256 of the slidelock 240 falls outside of the engagement zone 299.

It will be understood these are merely examples of the at least one engaging element, which are envisioned to be provided in different structural shapes and orientations, however they are preferably arranged to engage and disengage to lock or unlock the lower support orientation relative to the main support. The cover sandwiches the end portion of the lower support with the main support, and the cover and main support are preferably rigidly secured to one another to assure they do not move relative to one another unlike the lower support relative to the main support in the unlocked condition.

Referring to FIGS. 13 and 15A, the cover 216 may include hooks 252, as may the main support 204, to support an elastic band 254 suspended between the hook 252 and at least one of the hooks 246, 248 of the slidelock 240. The elastic band 254 assists in assuring the lock mechanism is biased in a locked condition. When the slidelock translates according to actuation by the lock mechanism to an unlocked condition that the elastic band is tensioned more than in the locked condition to form a spring return mechanism.

Figure 15B:
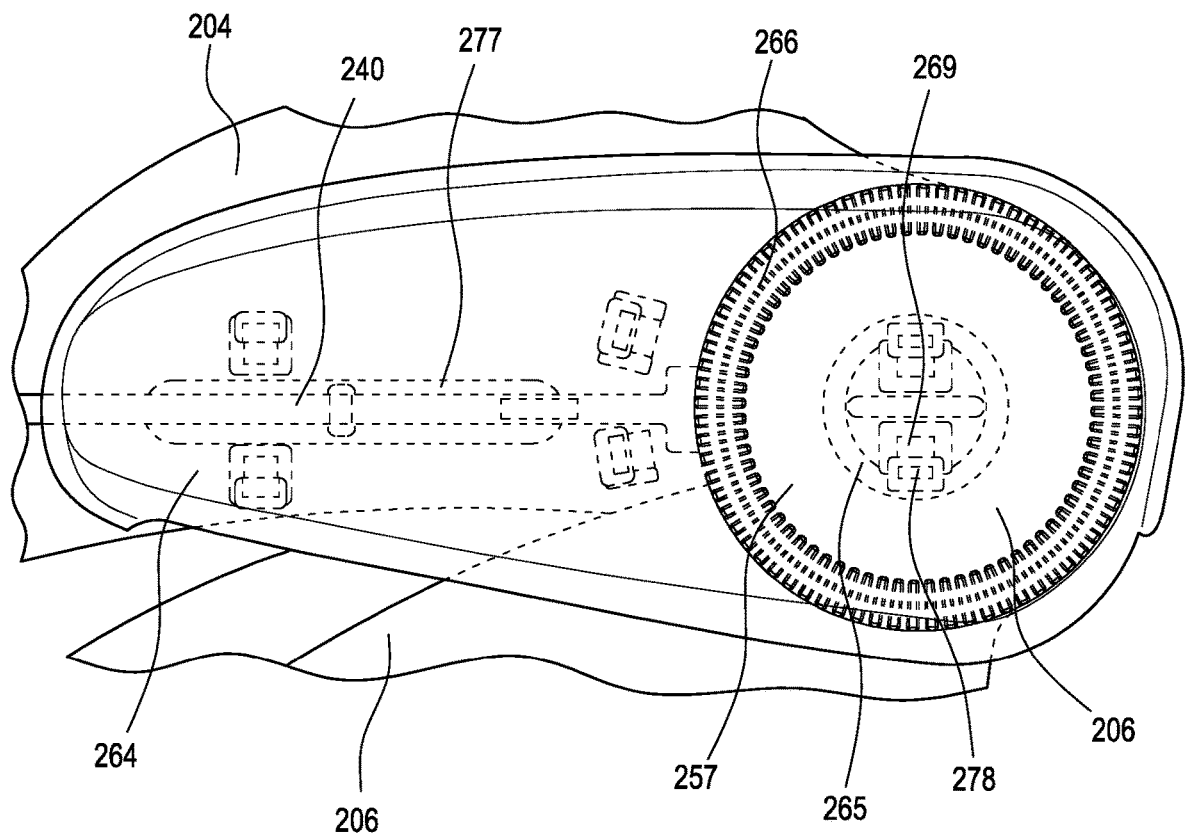
FIG. 15B is a schematic view of a variation of the side cover and main support in FIG. 15A.

FIG. 15B exemplifies a variation of a cover 264 arranged to fit to the main support 204 by posts 278 arranged for snapping. The main support 204 defines receptacles 269 configured and dimensioned to receive the posts 278 extending from the cover 264. The posts 278 are configured and dimensioned to flexibly extend through or into the receptacles 269 but deflect while pressed through the receptacles 269 to relax once having passed the opening to interlock with the main support 204. Various posts and receptacles are formed by the main support or the cover to interlock with one another.

In the variation of FIG. 15B, the main support 204 defines a boss 265 upon which the end portion 257 of lower support 206 rotates about. The boss 265 may have the receptacles 269 located therewithin to receive the posts 278.

As depicted in FIG. 15B, the end portion 257 defines a plurality of teeth 266 only disposed about a segment short of the entire circumference of the end portion 257 to define a range of rotation of the lower support 206 relative to the main support 204. It may be preferable to limit the rotation of the lower support to assure better selection of angles of the lower support relative to the upper support.

Either the cover 264 or the main support 204 may define at least one elongate guide 277 to guide the slidelock 240. The cover 264 or main support 204 may define an elongate slot for observing and facilitating movement of the slidelock 240, which may cooperate with the elongate guide 277.

In a variation of the embodiments described herein, different spring return mechanisms may be provided for a slidelock or elongate element, preferably so that once a user releases the lock mechanism, the spring return mechanism moves the lock mechanism back to the locked condition. The elongate element may include or have attached thereto a spring feature located at one of the end portions or along a length between the end portions arranged to deflect against a static boss located on the main support or other appropriate structure.

Figure 16A:
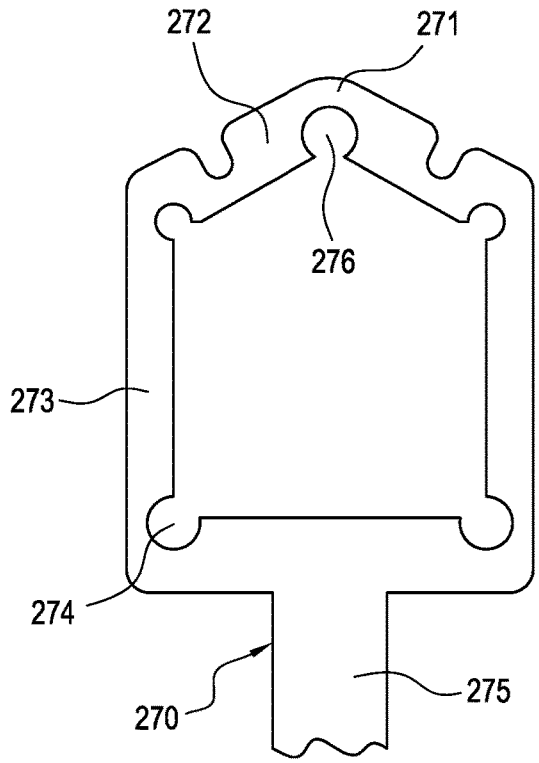
FIG. 16A is a schematic view of a variation of a paddle in a slidelock.
Figure 16B:
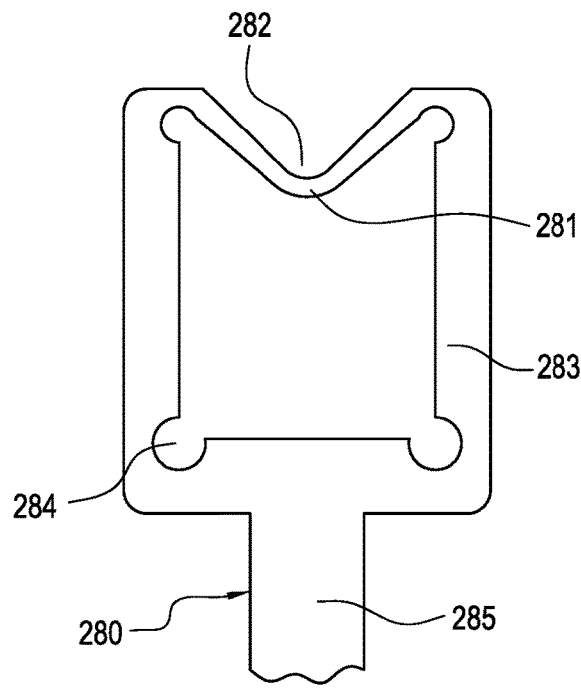
FIG. 16B is a schematic view of another variation of a paddle in a slidelock.

Referring to the examples of FIGS. 16A and 16B, a spring feature may be configured into the elongate element, either behind or ahead of the hinge. The spring feature may be connected to the elongate element as a separate component or be formed as part of the elongate element.

FIG. 16A depicts a slidelock 270 having a paddle 271 defining a compression spring feature 272 and extending from an arm 275. The paddle 271 defines a frame 273 arranged for compression upon sliding of the slidelock 270, such that the spring feature 272 protrudes outwardly from the frame relative to the arm 275. The frame 273 defines interior corner openings 274, 276 permitting it to be compressed upon activation of the slidelock. The top opening 276 may secure a fastener or pin to the frame 273 upon which the paddle 271 compresses.

FIG. 16B depicts a slidelock 280 having a paddle defining a tension spring feature 282 and extending from an arm 285. The paddle 281 defines a frame 283 arranged for tension upon sliding of the slidelock 280, such that the spring feature 282 protrudes inwardly from the frame toward the arm 285. The frame 283 defines interior corner openings 284 permitting the paddle 281 to be pulled into tension upon activation of the slidelock.

Figure 17:
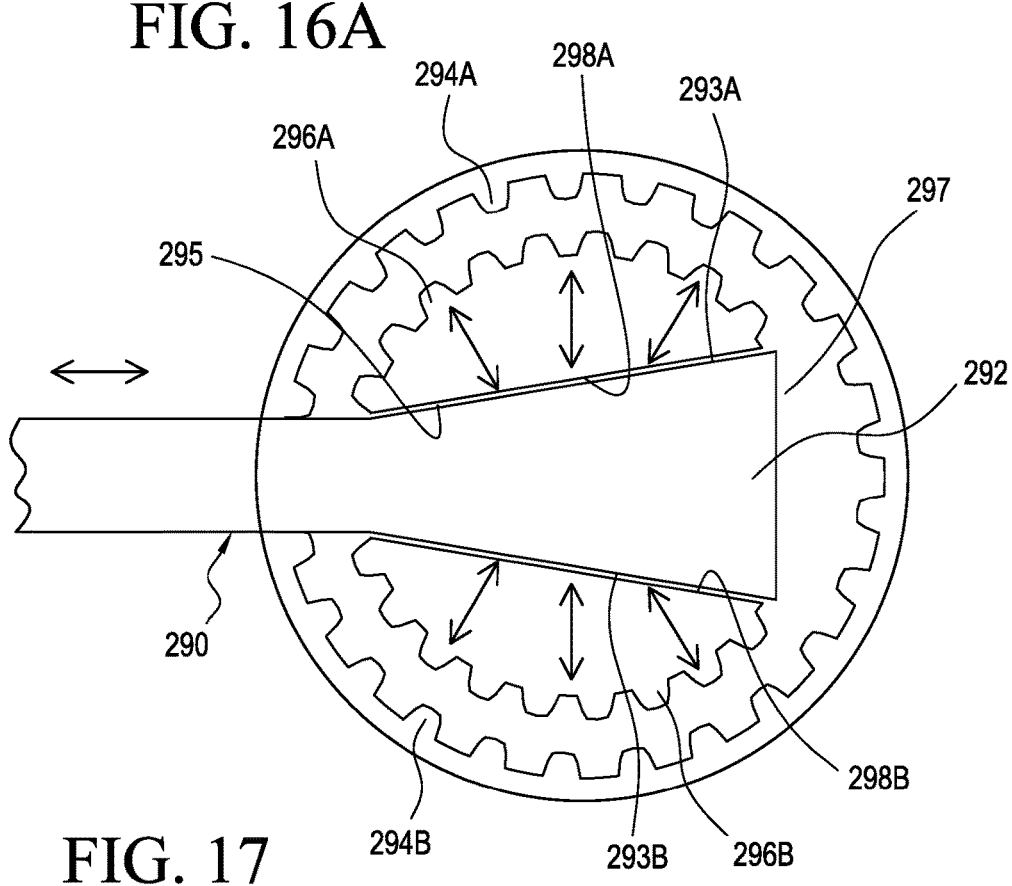
FIG. 17 is a schematic view of another variation of a slidelock system for use in a cervical collar.

FIG. 17 shows an alternate embodiment of a lock for the hinge which relies on a cam feature connected to or extending from the slidelock 290. The end portions of the main support and the lower support may include a plurality of peripheral teeth about their peripheries which are arranged to engage one another as the cam feature is urged against the main and lower supports end portions, such that the teeth mesh with one another to prevent movement of the hinge formed by the end portions of the main support and lower support.

One of the main support or lower support end portions is located concentrically with one another, and one generally within the periphery of the other. Both the main and lower supports may have an opening into which the cam feature can translate in and out of depending on the locking configuration of the lock mechanism. The main support defines interiorly facing teeth 294A, 294B located about an interior circumference, and the lower support defines at least one movable set of teeth 296A, 296B that are selectively engageable with the teeth 294A, 294B upon movement of the slidelock 290.

The at least one movable set of teeth 296A, 296B may include two blocks bearing the teeth along one side and along another side forming bearing surfaces 298A, 298B along which the slidelock 290 engages. The two movable sets of teeth 296A, 296B may form a first opening 295 into which the slidelock extends. The slidelock 290 forms a flared end 292 defining first and second sloped surfaces 293A, 293B engageable with the bearing surfaces 298A, 298B for moving the sets of teeth 296A, 296B relative to the teeth 294A, 294B. The sets of teeth 296A, 296B likewise form a second opening 297 through which the flared end 292 may be pushed through to reduce engagement of the sets of teeth 296A, 296B from the teeth 294A, 294B.

FIGS. 18A-18D represent another hinge connection 300 that may be useable in any of the cervical collar embodiments described herein, particularly with a lock mechanism. The hinge connection 300 includes a slidelock 302, an end portion 304 of a main support, an end portion 306 of a lower support, and a cam element 311 located between the end portions 304, 306, and in operative engagement with the slidelock 302. The cam element 311 includes at least one engaging element 316 of the slidelock 302 that is engageable with a corresponding at least one engaging element 326 of the end portion 306. In this example, the at least one engaging element 316 is a plurality of teeth 318, and the at least one engaging element 326 are radially extending teeth.

The slidelock 302 is linearly displaceable relative to the end portion 304, by at least one pin 308 and slot 310 connection. As shown, the slidelock 302 includes at least one pin 308 that is linearly slidable within a corresponding elongate slot 310. In the depicted embodiment, there are three pins 308 and three corresponding elongate slots 310.

Figure 18A:
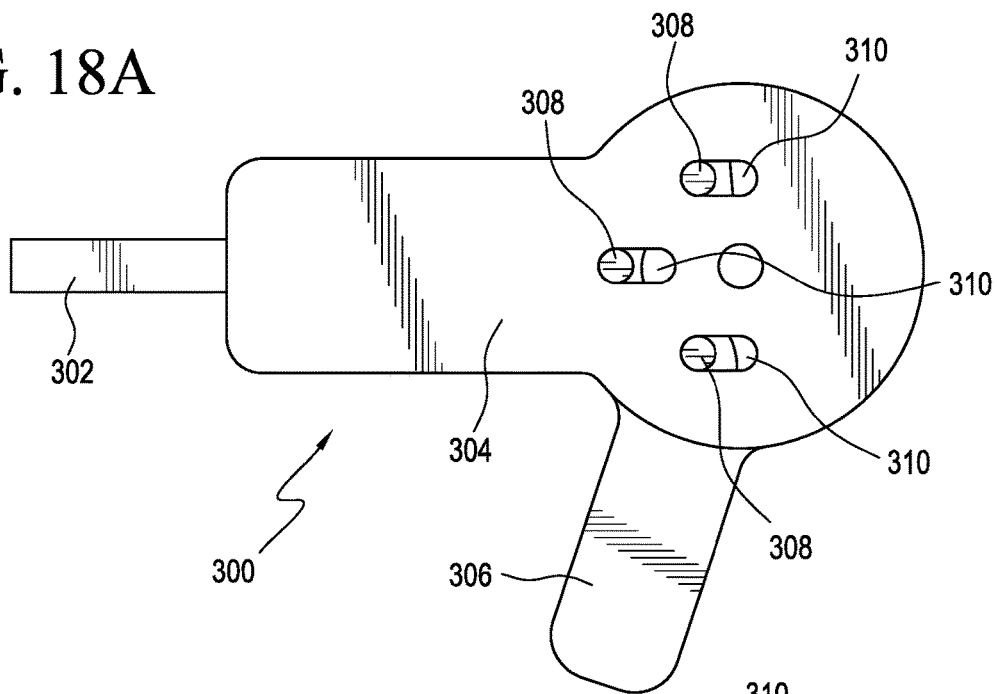
FIG. 18A is a schematic view of another variation of a slidelock system for use in a cervical collar.
Figure 18B:
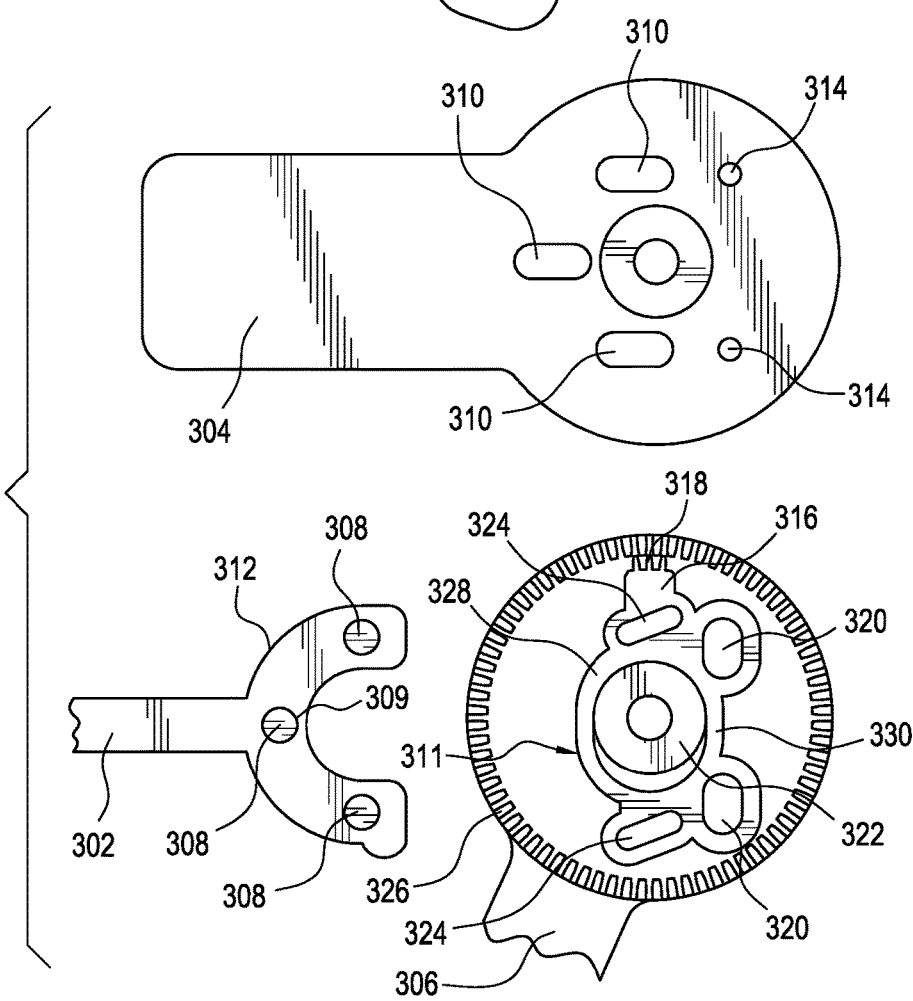
FIG. 18B is a schematic view of the slidelock system in FIG. 18A disassembled.

FIG. 18B shows the cam element 311 having rear openings 320 arranged to flexibly bias against a periphery of the end portion 306 when in an unlocked condition to urge retraction of the slidelock once released into a locked condition. The cam element 311 further defines front openings 324 spaced apart from a boss 322 defined by the end portion 306 upon which the end portion 304 rotates, and connected to one another from a front frame segment 328. The front and rear frame segments 328, 330 extend about the boss 322, and are adapted to be tensioned thereabout. The front openings 324 receive pins 309 extending oppositely to the at least one pin 308, and carried by arms 312 defined by the slidelock 302.

Figure 18C:
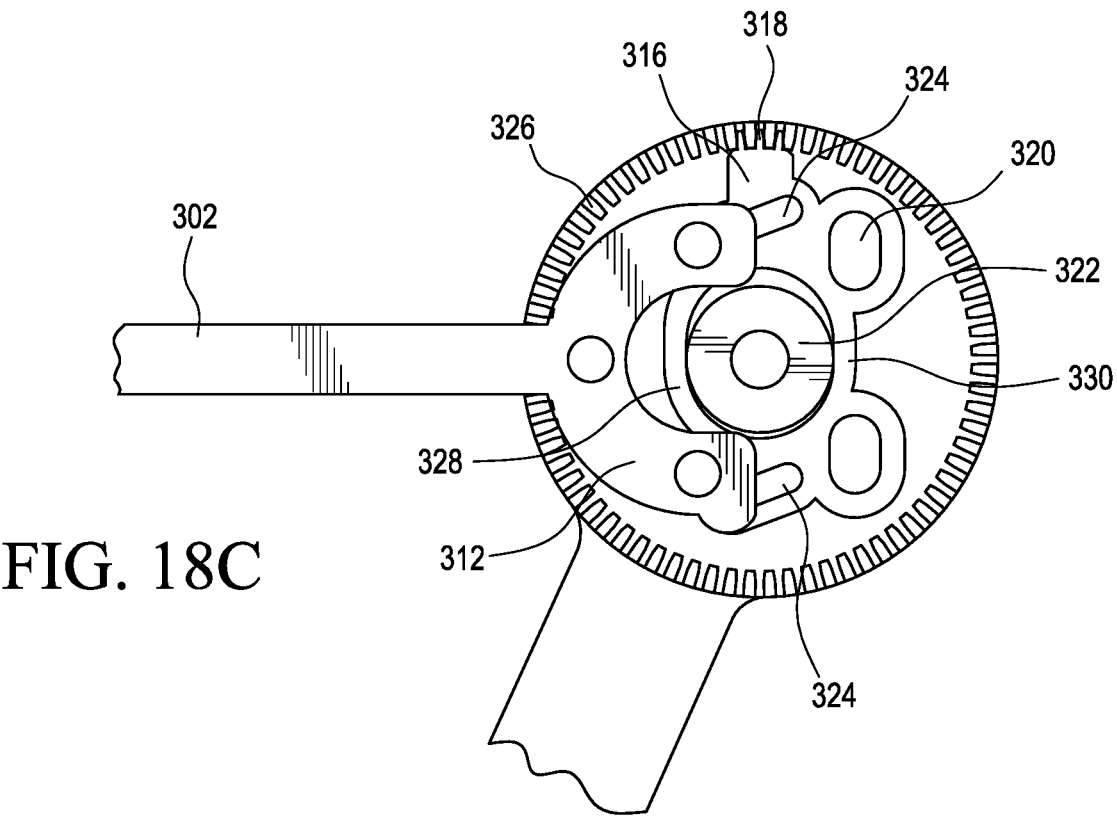
FIG. 18C is a schematic view of the slidelock system in FIG. 18A in a locked condition.
Figure 18D:
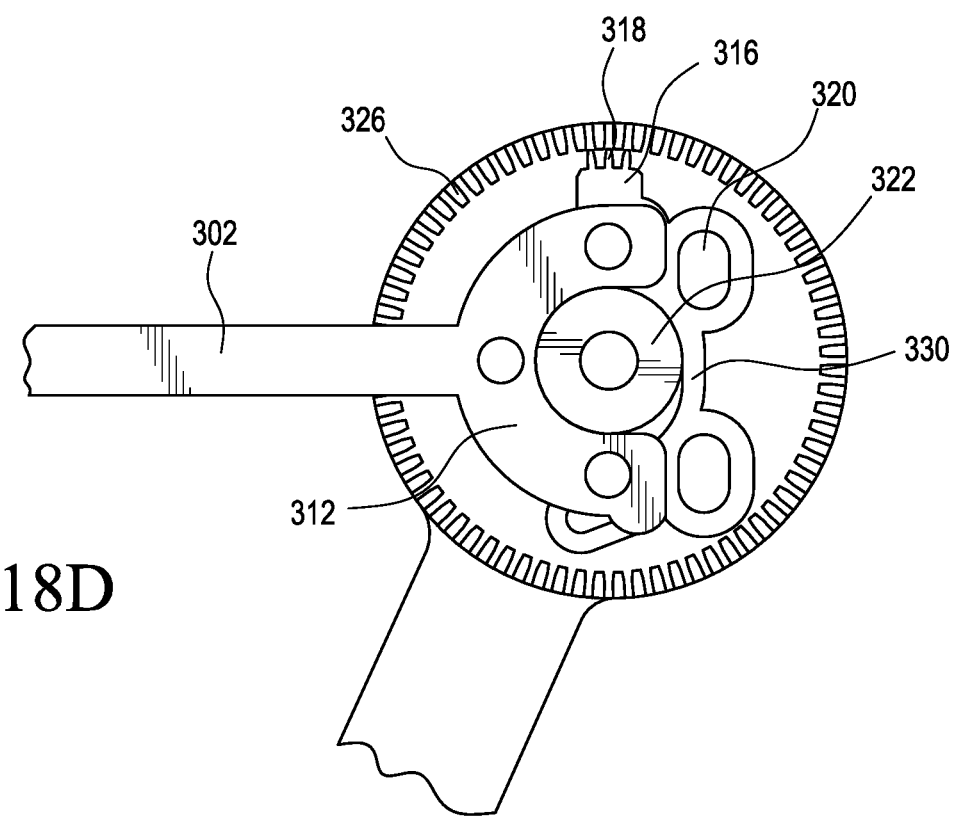
FIG. 18D is a schematic view of the slidelock system in FIG. 18A in an unlocked condition.

FIG. 18C shows the cam element 311 in a locked condition with the at least one engaging element 316 engaging the at least one engaging element 318. The cam element 311 is in a predetermined rest position, whereby the rear frame segment 328 is tensioned about the boss 322 to maintain the at least one engaging element 316 locked. FIG. 18D exemplifies the cam element 311 in an unlocked condition whereby the at least one engaging element 316 is pushed or pulled away from the at least one engaging element 318, and the front or rear frame segments 328, 330 are tensioned.

Figure 19A:
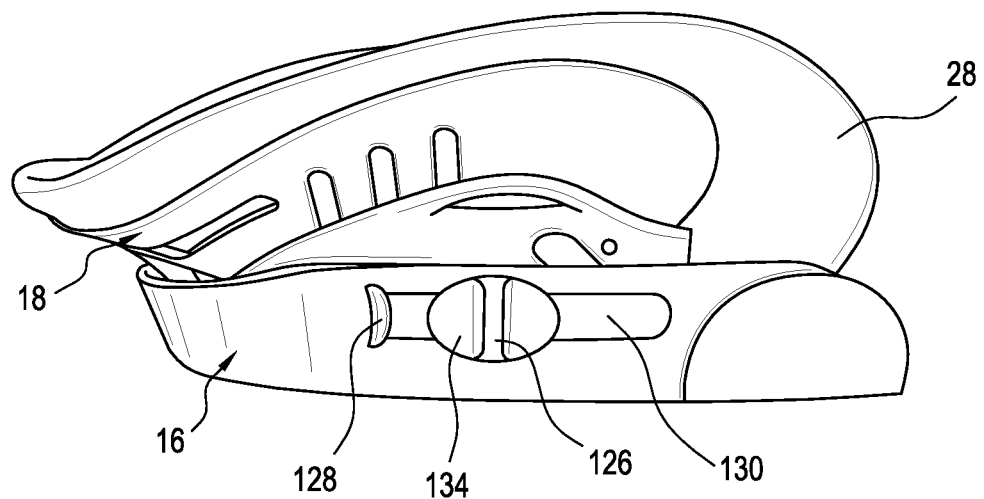
FIG. 19A is a schematic side elevational view of the upper support in the main support.
Figure 19B:
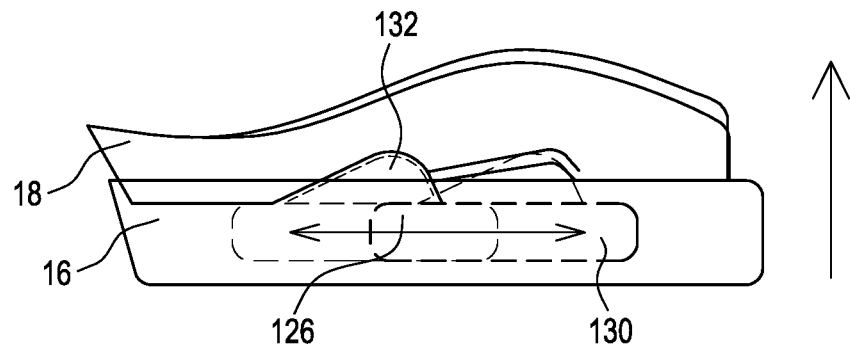
FIG. 19B is schematic view of the adjustability of the upper support relative to the main support in FIG. 19A.

Turning to FIGS. 19A-19B, the upper support 18 is slidably secured to the main support 16, such that continuous padding 28 is arranged about the main support 16. The upper support 18 can be locked in position relative to the main support 16, after adjusting the correct position. The main support 16 defines an elongate lateral slot 130 and the upper support 18 forms an elongate angled slot 132 arranged obliquely relative to the elongate slot 130 of the main support 16. A slider 126 slidably couples the main support 16 and the upper support 18 by the lateral and angled slots 128, 130. According to a variation, a knob of the slider may be rotated to unlock and lock the slider in a desired position. As seen from the components shown, the rotation my simply comprise a tight frictional fit of the slider against the main support 16 and the upper support 18. The lateral slot 130 is preferably arranged generally parallel to a length of the main support 16.

The main support 16 preferably defines a stationary element 128 proximate the lateral slot 130. The slider 126 has a tightening feature 134 for maintaining the lateral and angled slots in a relative position to another. Adjustment of the mandible angle could also be driven up/down through a simple rotating cam mechanism. The object is to elevate the posterior aspect of the chin tray to accommodate the slope of the mandible, thereby increasing stabilization against lateral movement of the head and C-Spine.

Figure 20:
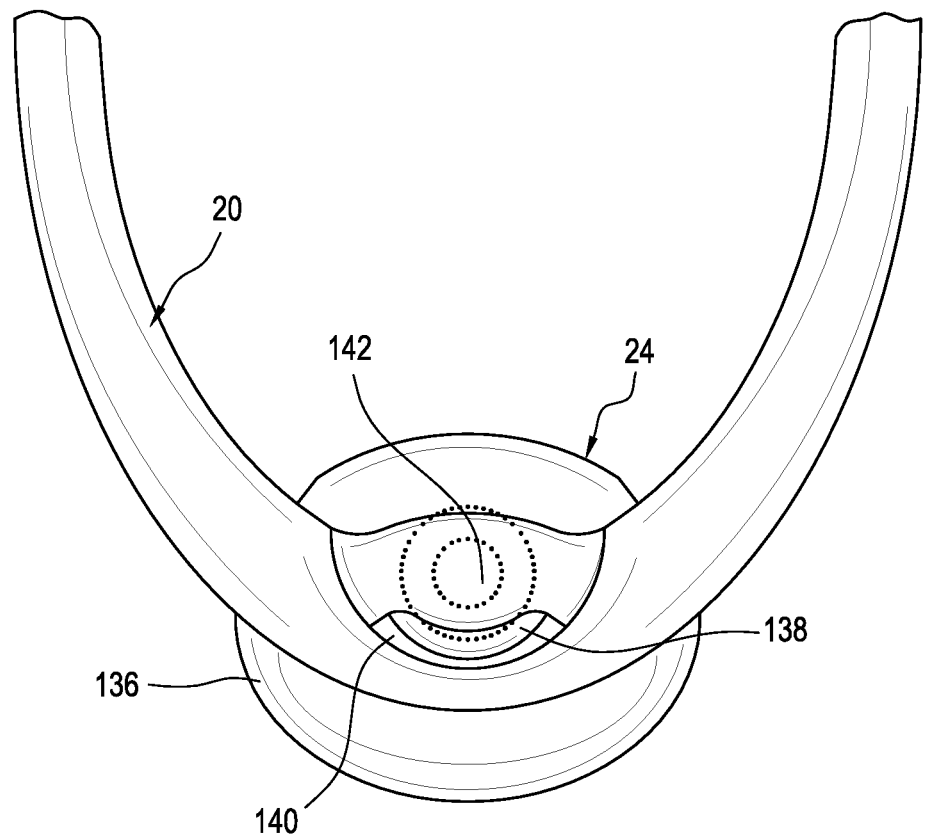
FIG. 20 is a plan view of the adjustment mechanism in FIG. 2A.
Figure 21:
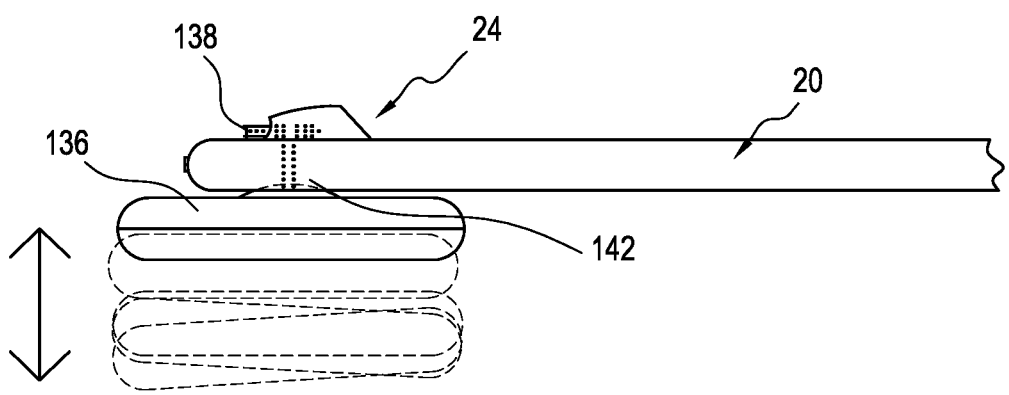
FIG. 21 is an elevational view of the adjustment mechanism of FIG. 20.

As in the embodiment of FIGS. 2A and 2B, and referring specifically to FIGS. 20 and 21, the adjustment mechanism 24 is located centrally along a lowermost portion of the lower support 20. The adjustment mechanism 24 has a sternal pad 136 adjustable in location relative to the lower support 20. The sternal pad 136 is mounted to a ball joint 142. The adjustment mechanism 24 has an adjustment dial and an extension element 144 arranged for adjustably extending relative to the lower support 20. The extension element 144 carries the ball joint 142 at an end thereof. The adjustment mechanism 24 includes a dial 138 for adjusting the length of the extension element 144 between the lower support 20 and the sternal pad 136. The dial 138 is accessible by a recess formed by the adjustment mechanism 24.

Figure 22A:
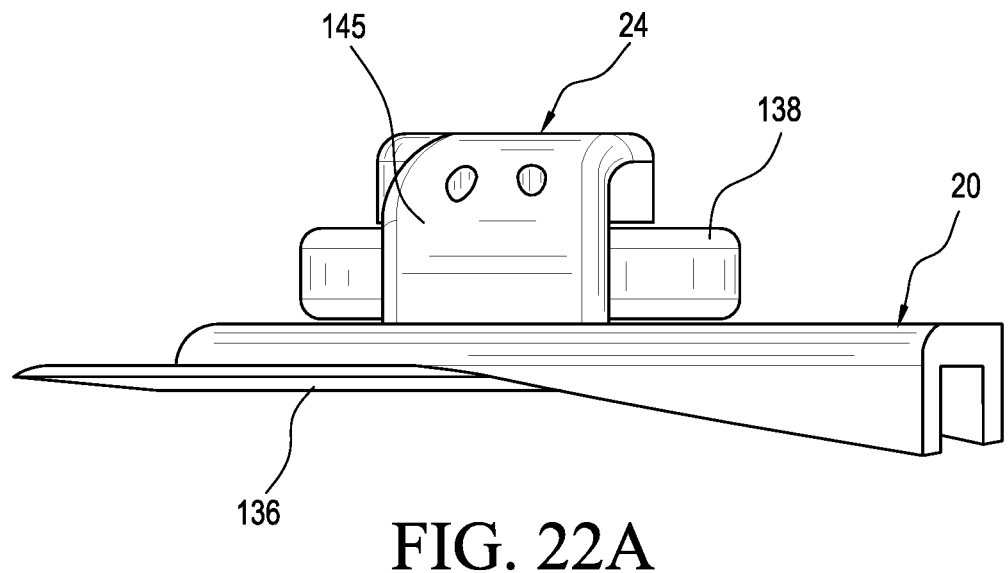
FIG. 22A is a schematic elevational view of the adjustment mechanism in a contracted configuration.
Figure 22B:
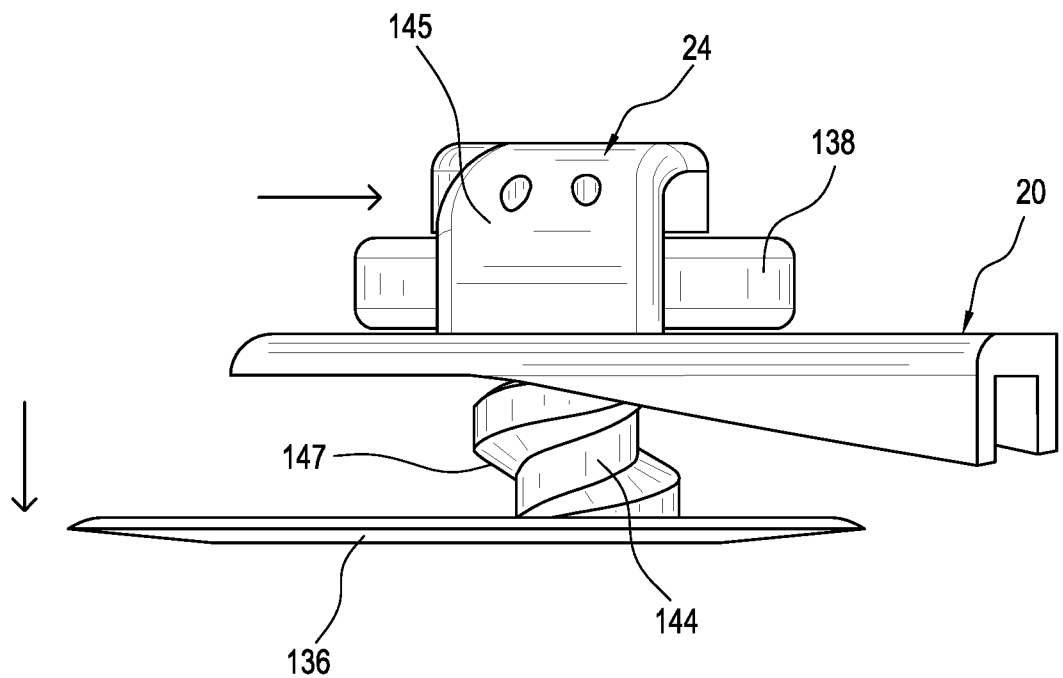
FIG. 22B is a schematic elevational view of the adjustment mechanism in an extended configuration.

FIGS. 22A and 22B show a variation of the adjustment mechanism 24 including a housing 145 arranged for receiving the extension element 144 in a contracted configuration resulting in a reduced or substantially minimized distance between the lower support and the sternal pad. The extension element 145 has a screw thread 147, and the housing 145 defines corresponding threads permitting slidable movement between the extension element 145 and the screw thread 147 according to adjustment of the dial 138.

Figure 23A:
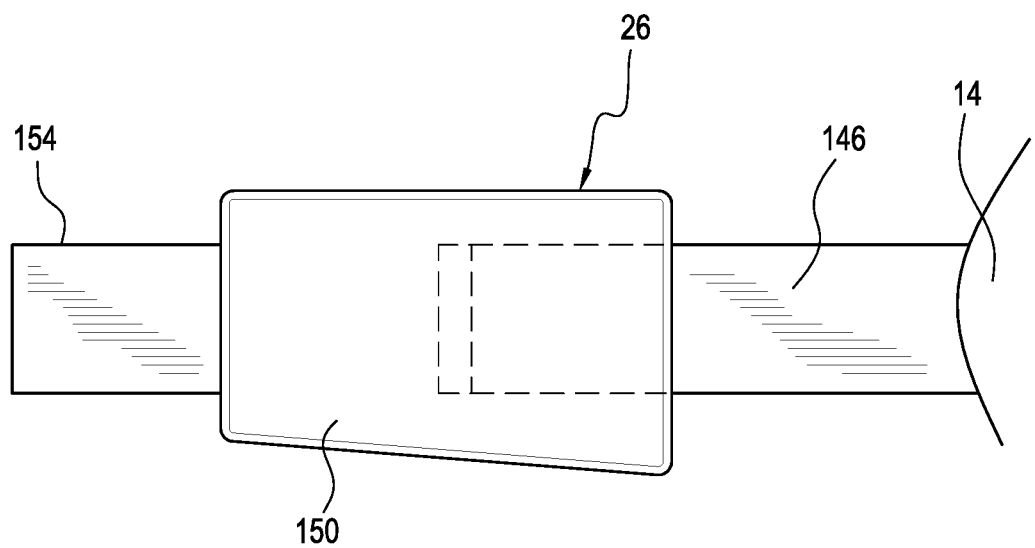
FIG. 23A is an elevational view of an embodiment of the connector in FIG. 2.
Figure 23B:
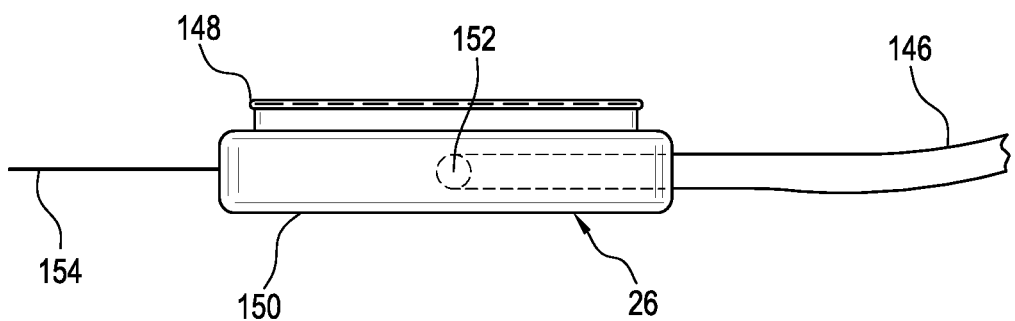
FIG. 23B is a top plan view of the connector in FIG. 23A.

As in the embodiment of FIGS. 2A and 2B, and referring to FIGS. 23A and 23B, a connector 26 connects the anterior component 12 to the posterior component 14. The connector 26 includes a base element 148 securing to a plate 150, and the base element 148 has a strap guide 152 about which a strap 146 extending from the posterior component 14 extends. The connector 26 has a pull tab 154 arranged for detaching the plate 150 from the base 148.

Figure 24A:
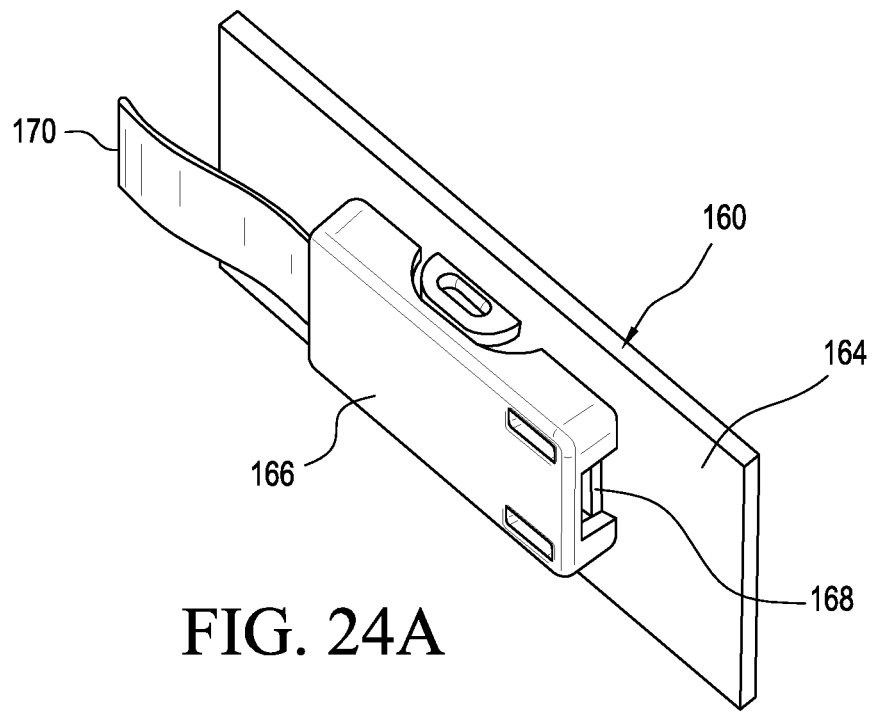
FIG. 24A is a perspective view of another embodiment of the connector in FIG. 2.
Figure 24B:
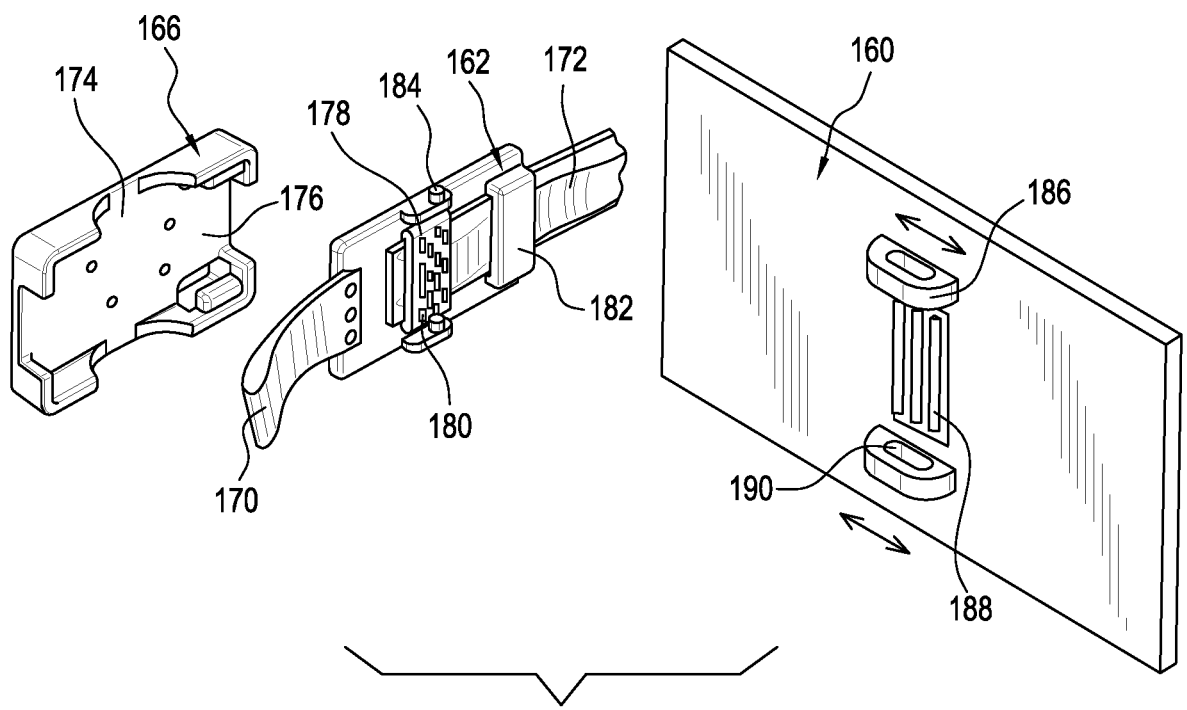
FIG. 24B is an exploded view of the connector in FIG. 24A.

FIGS. 24A and 24B display another embodiment of a connector 160 securing to a plate 164. A cap 166 is arranged to extend over the base element 162 and secure therewith. The connector 160 includes a pull tab 170 arranged for detaching the plate 160 from the base element 162 and the cap 166. The cap 166 defines an opening 168 with the plate 160 for permitting a strap 172 extending therethrough which secures to the posterior component. The base element 162 defines a platform 178 about which the strap 172 extends, and the platform 178 has at least one protuberance 180 over which the strap 172 extends.

The base element 162 further defines a channel guide 182 proximate to the opening 168 and through which the strap 172 extends. The base element 162 forms at least one detent 188 proximate to the at least one protuberance 180 for selective engagement of the strap 172 with the at least one protuberance 180. When the connector 160 is in a locked condition, the at least one protuberance 180 and the at least one detent 188 arrest the strap 172 from movement as they are urged against each other.

The plate 164 defines at least one retainer 186 having a channel 190 for selectively receiving a pin 184 protruding from the base element 162, such that the pin 184 slides within the channel 190 between locked and unlocked conditions of the connector 160. The cap 166 defines a side recess 174 for sliding the cap 166 and base element 162 relative to the plate 164 and permitting the at least one retainer 186 to move therewithin. The cap 166 defines a front recess 176 through which the strap 172 extends.

The features may be employed in different combinations from those shown in a cervical collar. While the foregoing embodiments have been described and shown, alternatives and modifications of these embodiments, such as those suggested by others, may be made to fall within the invention.

The invention claimed is:

1. A cervical collar having an anterior component arranged for connecting to a posterior component, the anterior component comprising:
a main support;
a lower support hingedly connected to the main support;
a sternum pad; and
an adjustment mechanism located on the lower support and the sternum pad is connected thereto such that the sternum pad is movable relative to the lower support;
wherein the sternum pad is mounted to a ball joint and the adjustment mechanism has an adjustment dial and an extension element arranged for adjustably extending relative to the lower support.

2. The cervical collar of claim 1, wherein the adjustment mechanism includes an extension element variably extendable from the adjustment mechanism.

3. The cervical collar of claim 2, wherein the adjustment mechanism includes a dial for adjusting a distance the extension element extends from the adjustment mechanism.

4. The cervical collar of claim 2, wherein the adjustment mechanism includes a housing arranged for receiving the extension element in a contracted configuration.

5. The cervical collar of claim 1, wherein the main support carries an upper support connected to inside the main support and oriented to face a mandible of a user.

6. The cervical collar of claim 5, wherein the upper support is maintained in a stationary relationship with the main support.

7. The cervical collar of claim 5, wherein the upper support is rigid.

8. The cervical collar of claim 1, wherein the adjustment mechanism is located at a lowermost portion of the lower support.

9. The cervical collar of claim 8, wherein the adjustment mechanism is located centrally at the lowermost portion of the lower support.

10. The cervical collar of claim 1, wherein the main support carries a lock mechanism for locking rotation of the lower support relative to the main support.

11. The cervical collar of claim 1, wherein the main support has a generally arcuate configuration adapted to extend about the mandible of a user, and the lower support has a generally arcuate configuration contoured for being adapted for securing against a sternum of the user.

12. A cervical collar having an anterior component arranged for connecting to a posterior component, the anterior component comprising:
a main support;
a lower support hingedly connected to the main support;
a sternum pad; and
an adjustment mechanism located on the lower support and the sternum pad is connected thereto such that the sternum pad is movable relative to the lower support;
wherein the adjustment mechanism includes a housing arranged for receiving an extension element in a contracted configuration resulting in a reduced or substantially minimized distance between the lower support and the sternum pad, the extension element having a screw thread, and the housing defining corresponding threads permitting slidable movement between the extension element and the screw thread according to adjustment of a dial associated with the extension element.

13. The cervical collar of claim 12, wherein the housing defines a recess from which at least a portion of the dial extends.

14. A cervical collar having an anterior component arranged for connecting to a posterior component, the anterior component comprising:
a main support;
a lower support hingedly connected to the main support;
a sternum pad; and
an adjustment mechanism located on the lower support and the sternum pad is connected thereto such that the sternum pad is movable relative to the lower support;
further comprising a lock mechanism for locking rotation of the lower support relative to the main support, the lock mechanism coupled to a slidelock arranged for operatively engaging end portions of the main support and lower support for locking and unlocking rotation of the lower support relative to the main support;

wherein the slidelock slides over an outer surface of the main support to cooperate with the main support to arrest or prevent rotation of the lower support relative to the main support.

15. The cervical collar of claim 14, wherein the slidelock defines a central rack of teeth arranged to correspond to and operatively engage elements forming part of the lock mechanism for enabling linear translation of the slidelock relative to the main support.

* * * * *